United States Patent
Schmitz et al.

(10) Patent No.: US 9,451,977 B2
(45) Date of Patent: Sep. 27, 2016

(54) MEMS MICRO DEBRIDER DEVICES AND METHODS OF TISSUE REMOVAL

(75) Inventors: Gregory P. Schmitz, Los Gatos, CA (US); Ming-Ting Wu, Northridge, CA (US); Richard T. Chen, Woodland Hills, CA (US); Arun Veeramani, Woodland Hills, CA (US)

(73) Assignee: Microfabrica Inc., Van Nuys, CA (US)

( * ) Notice: Subject to any disclaimer, the term of this patent is extended or adjusted under 35 U.S.C. 154(b) by 774 days.

(21) Appl. No.: 13/535,197

(22) Filed: Jun. 27, 2012

(65) Prior Publication Data
US 2013/0012975 A1  Jan. 10, 2013
US 2013/0331878 A2  Dec. 12, 2013

Related U.S. Application Data

(63) Continuation-in-part of application No. 13/007,578, filed on Jan. 14, 2011, now Pat. No. 8,795,278, which is a continuation-in-part of application No. 12/490,295, filed on Jun. 23, 2009, and a
(Continued)

(51) Int. Cl.
*A61B 17/32* (2006.01)
*A61B 17/16* (2006.01)
(Continued)

(52) U.S. Cl.
CPC ......... *A61B 17/32002* (2013.01); *A61B 17/16* (2013.01); *A61B 17/221* (2013.01);
(Continued)

(58) Field of Classification Search
CPC ............... A61B 17/16; A61B 17/1635; A61B 17/1671; A61B 17/16175; A61N 2017/1602

USPC ...................................................... 606/79–85
See application file for complete search history.

(56) References Cited

U.S. PATENT DOCUMENTS 1,179,910 A  4/1916  Greenfield
2,259,015 A  10/1941 Anderson et al.
(Continued)

FOREIGN PATENT DOCUMENTS

DE  202008013915 U  3/2009
EP  0572131 A1  12/1993
(Continued)

OTHER PUBLICATIONS

Schmitz et al.; U.S. Appl. No. 14/033,397 entitled "Micro-Mechanical Devices and Methods for Brain Tumor Removal," filed Sep. 20, 2013.
(Continued)

*Primary Examiner* — Nicholas Woodall
(74) *Attorney, Agent, or Firm* — Shay Glenn LLP

(57) ABSTRACT

Medical devices for shearing tissue into small pieces are provided. One exemplary device includes oppositely rotating first and second rotatable members, each located at least partially within a distal housing. The device also includes first and second circular axle portions, and first and second blades that are directly adjacent to one another and positioned to partially overlap such that tissue may be sheared between the first and second blades, between the first blade and the second axle portion and between the second blade and the first axle portion. The rotatable members are configured to engage tissue from a target tissue site with teeth of the first and second blades, rotate towards one another and inwardly to direct tissue from the target tissue site through a tissue engaging opening and into an interior portion of the distal housing. Methods of fabricating and using the above device are also disclosed.

14 Claims, 20 Drawing Sheets

Related U.S. Application Data continuation-in-part of application No. 12/490,301, filed on Jun. 23, 2009, now Pat. No. 8,475,458.

(60) Provisional application No. 61/408,558, filed on Oct. 29, 2010, provisional application No. 61/075,006, filed on Jun. 23, 2008, provisional application No. 61/164,864, filed on Mar. 30, 2009, provisional application No. 61/164,883, filed on Mar. 30, 2009, provisional application No. 61/075,006, filed on Jun. 23, 2008, provisional application No. 61/164,864, filed on Mar. 30, 2009, provisional application No. 61/164,883, filed on Mar. 30, 2009.

(51) Int. Cl.

| | | |
|---|---|---|
| *A61B 17/14* | (2006.01) | |
| *A61B 17/221* | (2006.01) | |
| *A61B 17/22* | (2006.01) | |
| *A61B 17/00* | (2006.01) | |
| *A61B 17/29* | (2006.01) | |
| *A61B 17/3207* | (2006.01) | |

(52) U.S. Cl.
CPC ............ *A61B 17/14* (2013.01); *A61B 17/1671* (2013.01); *A61B 17/22031* (2013.01); *A61B 90/361* (2016.02); *A61B 2017/003* (2013.01); *A61B 2017/00261* (2013.01); *A61B 2017/1602* (2013.01); *A61B 2017/22039* (2013.01); *A61B 2017/22044* (2013.01); *A61B 2017/22077* (2013.01); *A61B 2017/2927* (2013.01); *A61B 2017/32004* (2013.01); *A61B 2017/32006* (2013.01); *A61B 2017/320032* (2013.01); *A61B 2017/320048* (2013.01); *A61B 2017/320775* (2013.01)

(56) References Cited

U.S. PATENT DOCUMENTS

| | | |
|---|---|---|
| 2,455,655 A | 12/1948 | Carroll |
| 3,404,677 A | 10/1968 | Springer |
| 3,882,872 A | 5/1975 | Douvas et al. |
| 3,937,222 A | 2/1976 | Banko |
| 4,197,645 A | 4/1980 | Schiecher |
| 4,334,650 A * | 6/1982 | Hardwick et al. ............ 241/236 |
| 4,598,710 A | 7/1986 | Kleinberg et al. |
| 4,621,637 A | 11/1986 | Fishbein |
| 4,747,821 A | 5/1988 | Kensey et al. |
| 4,804,364 A | 2/1989 | Dieras et al. |
| 4,842,578 A | 6/1989 | Johnson et al. |
| 4,844,363 A | 7/1989 | Garnier et al. |
| 4,854,808 A | 8/1989 | Bisiach |
| 4,943,296 A | 7/1990 | Funakubo et al. |
| 4,983,179 A | 1/1991 | Sjostrom |
| 4,986,807 A | 1/1991 | Farr |
| 5,019,088 A | 5/1991 | Farr |
| 5,084,052 A | 1/1992 | Jacobs |
| 5,141,168 A | 8/1992 | Pepper |
| 5,160,095 A * | 11/1992 | Pepper ....................... 241/46.06 |
| 5,181,433 A | 1/1993 | Ueno et al. |
| 5,190,637 A | 3/1993 | Guckel |
| 5,226,909 A | 7/1993 | Evans et al. |
| 5,284,486 A | 2/1994 | Kotula et al. |
| 5,378,583 A | 1/1995 | Guckel et al. |
| 5,411,511 A | 5/1995 | Hall |
| 5,465,444 A | 11/1995 | Bigler et al. |
| 5,484,112 A | 1/1996 | Koenig |
| 5,496,668 A | 3/1996 | Guckel et al. |
| 5,522,829 A | 6/1996 | Michalos |
| 5,549,637 A | 8/1996 | Crainich |
| 5,575,799 A | 11/1996 | Bolanos et al. |
| 5,576,147 A | 11/1996 | Guckel et al. |
| 5,591,187 A | 1/1997 | Dekel |
| 5,601,556 A | 2/1997 | Pisharodi |
| 5,618,293 A | 4/1997 | Sample et al. |
| 5,643,304 A | 7/1997 | Schechter et al. |
| 5,662,284 A | 9/1997 | Koenig |
| 5,676,321 A | 10/1997 | Kroger |
| 5,685,838 A | 11/1997 | Peters et al. |
| 5,695,510 A | 12/1997 | Hood |
| 5,718,618 A | 2/1998 | Guckel et al. |
| 5,725,530 A | 3/1998 | Popken |
| 5,779,713 A | 7/1998 | Turjanski et al. |
| 5,782,848 A | 7/1998 | Lennox |
| 5,788,169 A | 8/1998 | Koenig |
| 5,810,809 A | 9/1998 | Rydell |
| 5,823,990 A | 10/1998 | Henley |
| 5,846,244 A | 12/1998 | Cripe |
| 5,863,294 A | 1/1999 | Alden |
| 5,866,281 A | 2/1999 | Guckel et al. |
| 5,908,719 A | 6/1999 | Guckel et al. |
| 5,910,150 A | 6/1999 | Saadat |
| 5,916,231 A | 6/1999 | Bays |
| 5,928,158 A | 7/1999 | Aristides |
| 5,928,161 A | 7/1999 | Krulevitch et al. |
| 5,957,881 A | 9/1999 | Peters et al. |
| 6,001,112 A | 12/1999 | Taylor |
| 6,010,477 A | 1/2000 | Bays |
| 6,013,991 A | 1/2000 | Philipp |
| 6,027,630 A | 2/2000 | Cohen |
| 6,063,088 A | 5/2000 | Winslow |
| 6,129,698 A | 10/2000 | Beck |
| 6,217,598 B1 | 4/2001 | Berman |
| 6,221,088 B1 | 4/2001 | Bays |
| 6,238,405 B1 | 5/2001 | Findlay et al. |
| 6,293,957 B1 | 9/2001 | Peters et al. |
| 6,447,525 B2 | 9/2002 | Follmer et al. |
| 6,454,717 B1 | 9/2002 | Pantages et al. |
| 6,475,369 B1 | 11/2002 | Cohen |
| 6,503,263 B2 | 1/2003 | Adams |
| 6,517,544 B1 | 2/2003 | Michelson |
| 6,565,588 B1 | 5/2003 | Clement et al. |
| 6,572,613 B1 | 6/2003 | Ellman et al. |
| 6,572,742 B1 | 6/2003 | Cohen |
| 6,613,972 B2 | 9/2003 | Cohen et al. |
| 6,663,031 B2 | 12/2003 | Henderson et al. |
| 6,666,874 B2 | 12/2003 | Heitzmann et al. |
| 6,753,952 B1 | 6/2004 | Lawrence et al. |
| 6,761,723 B2 | 7/2004 | Buttermann et al. |
| 6,790,377 B1 | 9/2004 | Cohen |
| 6,951,456 B2 | 10/2005 | Cohen et al. |
| 6,994,708 B2 | 2/2006 | Manzo |
| 7,052,494 B2 | 5/2006 | Goble et al. |
| 7,160,304 B2 | 1/2007 | Michelson |
| 7,163,614 B2 | 1/2007 | Cohen |
| 7,195,989 B2 | 3/2007 | Lockard et al. |
| 7,229,544 B2 | 6/2007 | Cohen |
| 7,235,088 B2 | 6/2007 | Pinto et al. |
| 7,239,219 B2 | 7/2007 | Brown et al. |
| 7,252,861 B2 | 8/2007 | Smalley |
| 7,479,147 B2 | 1/2009 | Honeycutt et al. |
| 7,540,867 B2 | 6/2009 | Jinno et al. |
| 7,553,307 B2 | 6/2009 | Bleich et al. |
| 7,699,790 B2 | 4/2010 | Simpson |
| 7,918,849 B2 | 4/2011 | Bleich et al. |
| 8,002,776 B2 | 8/2011 | Liu et al. |
| 8,034,003 B2 | 10/2011 | Pesce et al. |
| 8,114,074 B1 | 2/2012 | Slater |
| 8,292,889 B2 | 10/2012 | Cunningham et al. |
| 8,326,414 B2 | 12/2012 | Neubardt et al. |
| 8,409,235 B2 | 4/2013 | Rubin |
| 8,414,606 B2 | 4/2013 | Shadeck et al. |
| 8,486,096 B2 | 7/2013 | Robertson et al. |
| 8,512,342 B2 | 8/2013 | Meredith |
| 2001/0000531 A1 | 4/2001 | Casscells et al. |
| 2001/0041307 A1 | 11/2001 | Lee et al. |
| 2002/0058944 A1 | 5/2002 | Michelson |
| 2002/0099367 A1 | 7/2002 | Guo et al. |
| 2002/0123763 A1 | 9/2002 | Blake |
| 2002/0138088 A1 | 9/2002 | Nash et al. |
| 2003/0144681 A1 | 7/2003 | Sample |
| 2003/0163126 A1 | 8/2003 | West |

(56) References Cited

U.S. PATENT DOCUMENTS

| | | |
|---|---|---|
| 2003/0179364 A1 | 9/2003 | Steenblik et al. |
| 2004/0138672 A1 | 7/2004 | Michelson |
| 2005/0021065 A1 | 1/2005 | Yamada et al. |
| 2005/0029109 A1 | 2/2005 | Zhang et al. |
| 2005/0054972 A1 | 3/2005 | Adams et al. |
| 2005/0059905 A1 | 3/2005 | Boock et al. |
| 2005/0090848 A1 | 4/2005 | Adams |
| 2005/0222598 A1 | 10/2005 | Ho et al. |
| 2006/0089662 A1 | 4/2006 | Davison et al. |
| 2006/0161185 A1 | 7/2006 | Saadat et al. |
| 2006/0184175 A1 | 8/2006 | Schomer et al. |
| 2006/0200152 A1 | 9/2006 | Karubian et al. |
| 2006/0212060 A1 | 9/2006 | Hacker et al. |
| 2006/0217730 A1 | 9/2006 | Termanini |
| 2006/0224160 A1 | 10/2006 | Trieu et al. |
| 2006/0229624 A1 | 10/2006 | May et al. |
| 2006/0229646 A1 | 10/2006 | Sparks |
| 2006/0241566 A1 | 10/2006 | Moon et al. |
| 2006/0276782 A1 | 12/2006 | Gedebou |
| 2006/0282065 A1 | 12/2006 | Cohen |
| 2007/0073303 A1 | 3/2007 | Namba |
| 2007/0100361 A1 | 5/2007 | Cohen |
| 2007/0162062 A1 | 7/2007 | Norton et al. |
| 2007/0173872 A1 | 7/2007 | Neuenfeldt |
| 2007/0197895 A1 | 8/2007 | Nycz et al. |
| 2007/0198038 A1 | 8/2007 | Cohen et al. |
| 2007/0219459 A1 | 9/2007 | Cohen |
| 2007/0260253 A1 | 11/2007 | Johnson et al. |
| 2007/0265648 A1 | 11/2007 | Cohen |
| 2008/0004643 A1 | 1/2008 | To et al. |
| 2008/0009697 A1 | 1/2008 | Haider et al. |
| 2008/0065125 A1 | 3/2008 | Olson |
| 2008/0091074 A1 | 4/2008 | Kumar et al. |
| 2008/0091224 A1 | 4/2008 | Griffis et al. |
| 2008/0103504 A1 | 5/2008 | Schmitz et al. |
| 2008/0161809 A1 | 7/2008 | Schmitz et al. |
| 2008/0249553 A1 | 10/2008 | Gruber et al. |
| 2009/0012524 A1 | 1/2009 | Dower |
| 2009/0018565 A1 | 1/2009 | To et al. |
| 2009/0018566 A1 | 1/2009 | Escudero et al. |
| 2009/0124975 A1 | 5/2009 | Oliver et al. |
| 2009/0228030 A1 | 9/2009 | Shadeck |
| 2009/0234378 A1 | 9/2009 | Escudero et al. |
| 2009/0270812 A1 | 10/2009 | Litscher et al. |
| 2009/0306773 A1 | 12/2009 | Silvestrini et al. |
| 2010/0010492 A1 | 1/2010 | Lockard et al. |
| 2010/0010525 A1 | 1/2010 | Lockard et al. |
| 2010/0030216 A1 | 2/2010 | Arcenio |
| 2010/0094320 A1 | 4/2010 | Arat et al. |
| 2010/0152758 A1 | 6/2010 | Mark et al. |
| 2010/0160916 A1 | 6/2010 | Chana et al. |
| 2010/0191266 A1 | 7/2010 | Oliver et al. |
| 2010/0217268 A1 | 8/2010 | Bloebaum et al. |
| 2010/0305595 A1 | 12/2010 | Hermann |
| 2011/0112563 A1 | 5/2011 | To et al. |
| 2011/0190738 A1 | 8/2011 | Zemlok et al. |
| 2011/0230727 A1 | 9/2011 | Sanders et al. |
| 2011/0288573 A1 | 11/2011 | Yates et al. |
| 2012/0041263 A1 | 2/2012 | Sholev |
| 2012/0053606 A1 | 3/2012 | Schmitz et al. |
| 2012/0071752 A1 | 3/2012 | Sewell et al. |
| 2012/0109024 A1 | 5/2012 | Theuer |
| 2012/0109172 A1 | 5/2012 | Schmitz et al. |
| 2012/0178985 A1 | 7/2012 | Walters et al. |
| 2012/0191116 A1 | 7/2012 | Fylnn et al. |
| 2012/0191121 A1 | 7/2012 | Chen et al. |
| 2012/0221035 A1 | 8/2012 | Harvey |
| 2013/0226209 A1 | 8/2013 | Lockard et al. |
| 2014/0350567 A1 | 11/2014 | Schmitz et al. |
| 2015/0173788 A1 | 6/2015 | Lockard et al. |

FOREIGN PATENT DOCUMENTS

| | | |
|---|---|---|
| EP | 0925857 A2 | 6/1999 |
| EP | 1256319 A2 | 11/2002 |
| EP | 1026996 B1 | 10/2007 |
| WO | WO93/05719 A1 | 4/1993 |
| WO | WO99/63891 A1 | 12/1999 |
| WO | WO02/49518 A2 | 6/2002 |
| WO | WO02/062226 A1 | 8/2002 |
| WO | WO2004/069498 A2 | 8/2004 |
| WO | WO 2008/037984 A2 | 4/2008 |
| WO | WO 2012/040432 A1 | 3/2012 |

OTHER PUBLICATIONS

Chen et al.; U.S. Appl. No. 14/181,247 entitled "Concentric Cutting Devices for Use in Minimally Invasive Medical Procedures," filed Feb. 14, 2014.

Schmitz et al.; U.S. Appl. No. 14/333,458 entitled "Counterfeiting deterrent and security devices, systems, and methods," filed Jul. 16, 2014.

Schmitz et al.; U.S. Appl. No. 13/659,734 entitled "Minimally Invasive Micro Tissue Debriders Having Targeted Rotor Positions," filed Oct. 24, 2012.

Schmitz et al.; U.S. Appl. No. 13/714,285 entitled "Micro Debrider Devices and Methods of Tissue Removal," filed Dec. 13, 2012.

Schmitz et al.; U.S. Appl. No. 13/843,462 entitled "MEMS Debrider Drive Train," filed Mar. 15, 2013.

Schmitz et al.; U.S. Appl. No. 13/855,627 entitled "Micro-articulated surgical instruments using micro gear actuation," filed Apr. 2, 2013.

Cohen et al.; EFAB: Batch production of functional, fully-dense metal parts with micron-scale features; Proc 9th, Solid Freeform Fabrication; Univ. of Texas at Austin; pp. 161-168; Aug. 1998.

Cohen et al.; EFAB: low-cost automated electrochemical batch fabrication of arbitrary 3-D microstructures; Micromachining and Microfabrication Process Technology, SPIE 1999 Symposium on Micromachining and Microfabrication; 11 pgs.; Sep. 1999.

Cohen et al.; EFAB: Rapid, low-cost desktop micromachining of high aspect ratio true 3-D MEMS; Proc. 12th, IEEE Micro Electro Mechanical Systems Workshop; IEEE; pp. 244-251; Jan. 1999.

Cohen, Adam L.; 3-D micromachining by electrochemical fabrication; Micromachine Devices; pp. 6-7; Mar. 1999.

Cohen, Adam L.; Electrochemical Fabrication (EFAB}); MEMS Handbook; Chapter 19; CRC Press LLC; pp. 19-1-19-23; Jan. 7, 2002.

Microfabrication—rapid prototyping's killer application; Rapid Prototyping Report; vol. 9; No. 6; pp. 1-5; Jun. 1999.

SSI Shredding Systems; www.ssiworld.com; 16 pgs.; Sep. 24, 2009 (downloaded).

Tseng et al.; EFAB: high aspect ratio, arbitrary 3-D metal microstructures using a low-cost automated batch process; 3rd Int'l. Workshop on High Aspect Ratio Microstructure Technology (HARMST99); Kazusa, Japan; 4 pgs.; Jun. 1999.

Tseng et al.; EFAB: high aspect ratio, arbitrary 3-D metal microstructures using a low-cost automated batch process; Microelectromechanical Systems (MEMS); vol. 1; ASME 1999 (Int'l. Mechanical Engineering Congress and Exposition; 6 pgs.; Nov. 1999.

Zhang et al.; EFAB: rapid desktop manufacturing of true 3-D microstructures; Proc. 2nd Int'l. Conf. on Integrated MicroNanotechnology for Space Applications; The Aerospace Co.; 11 pgs.; Apr. 1999.

Lockard et al.; U.S. Appl. No. 12/491,220 entitled "Miniature Shredding Tool for Use in Medical Applications and Methods for Making," filed Jun. 24, 2009.

Jho et al.; Endoscopy assisted transsphenoidal surgery for pituitary adenoma; Acta Neurochirurgica; 138 (12); pp. 1416-1425; 1996 (year of pub. sufficiently earlier than effective US filing date and any foreign priority date).

Schmitz et al.; U.S. Appl. No. 14/440,088 entitled "Micro-mechanical device and method for obstructive sleep apnea treatment," filed May 1, 2015.

Bovie Medical Corporation; Resistick II(TM) Coated Electrodes (product information); 2 pgs.; retrieved from the internet (http://www.boviemedical.com/products_aaronresistickelect.asp); print/retrieval date: Apr. 6, 2016.

* cited by examiner

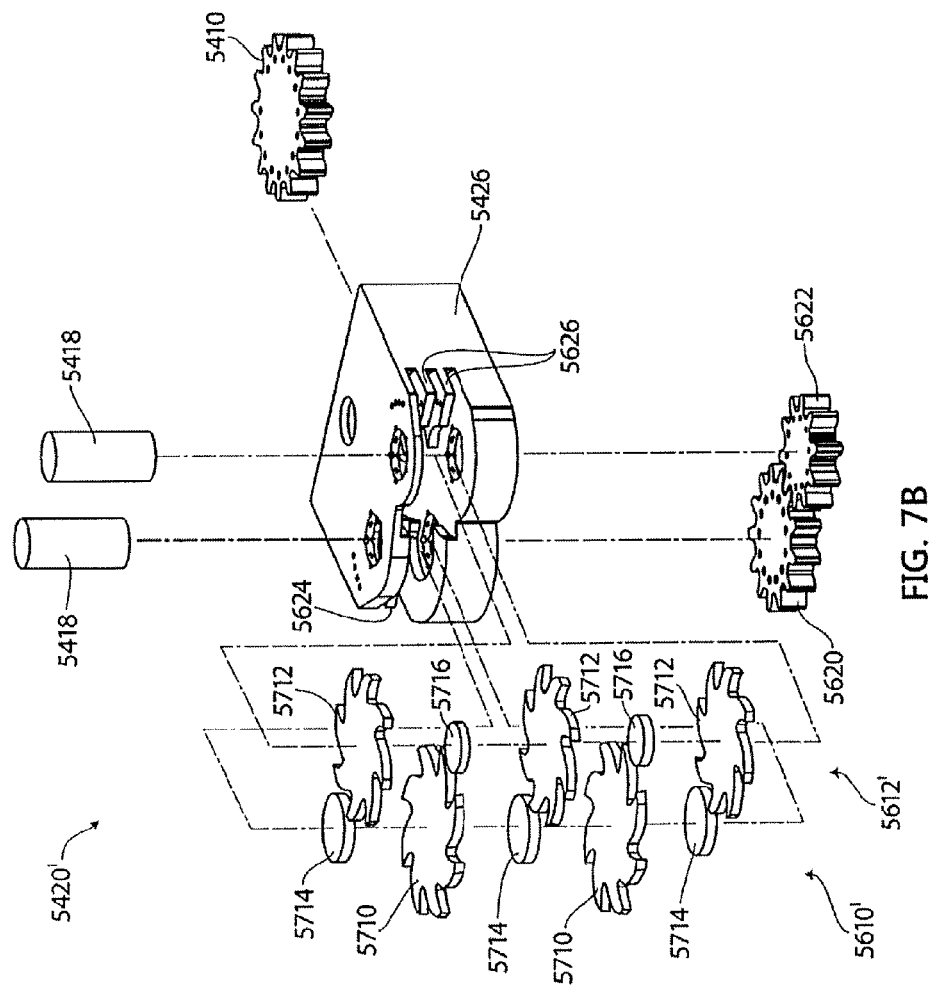

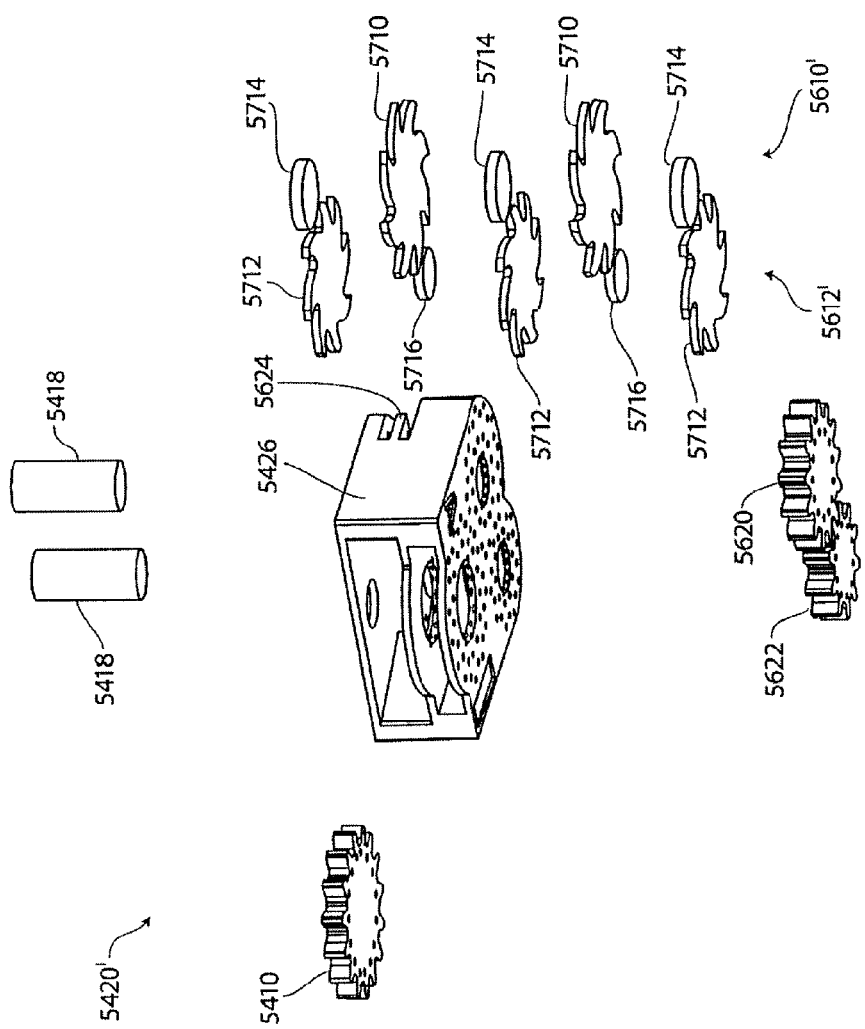

MEMS MICRO DEBRIDER DEVICES AND METHODS OF TISSUE REMOVAL

CROSS REFERENCE TO RELATED APPLICATIONS

This application is a Continuation-In-Part of U.S. application Ser. No. 13/007,578 filed Jan. 14, 2011, which claims the benefit of U.S. Provisional Application No. 61/408,558 filed Oct. 29, 2010; and which is a Continuation-In-Part of U.S. application Ser. No. 12/490,295 filed Jun. 23, 2009, which claims priority to: U.S. Provisional Application No. 61/075,006 filed Jun. 23, 2008; U.S. Provisional Application No. 61/164,864 filed Mar. 30, 2009; and U.S. Provisional Application No. 61/164,883 filed Mar. 30, 2009. This application is a Continuation of U.S. application Ser. No. 13/007,578 filed Jan. 14, 2011, which is also a Continuation in Part of U.S. application Ser. No. 12/490,301 filed Jun. 23, 2009 which claims priority to: U.S. Provisional Application No. 61/075,006 filed Jun. 23, 2008; U.S. Provisional Application No. 61/164,864 filed Mar. 30, 2009; and U.S. Provisional Application No. 61/164,883 filed Mar. 30, 2009. Each of these applications is incorporated herein by reference as if set forth in full herein.

INCORPORATION BY REFERENCE

All publications and patent applications mentioned in this specification are herein incorporated by reference to the same extent as if each individual publication or patent application was specifically and individually indicated to be incorporated by reference.

FIELD OF THE INVENTION

Embodiments of the present disclosure relate to micro-scale and millimeter-scale tissue debridement devices that may, for example, be used to remove unwanted tissue or other material from selected locations within a body of a patient during a minimally invasive or other medical procedure and in particular embodiments multi-layer, multi-material electrochemical fabrication methods are used to, in whole or in part, form such devices.

BACKGROUND OF THE INVENTION

Debridement is the medical removal of necrotic, cancerous, damaged, infected or otherwise unwanted tissue. Some medical procedures include, or consist primarily of, the mechanical debridement of tissue from a subject. Rotary debrider devices have been used in such procedures for many years.

Some debrider devices with relatively large dimensions risk removing unintended tissue from the subject, or damaging the unintended tissue. There is a need for tissue removal devices which have small dimensions and improved functionality which allow them to more safely remove only the desired tissue from the patient. There is also a need for tissue removal devices which have small dimensions and improved functionality over existing products and procedures which allow them to more efficiently remove tissue from the patient.

Prior art tissue removal devices often remove tissue in large pieces, having dimensions well over 2 mm. The tissue pieces are removed through an aspiration lumen typically 3.5 to 5 mm in diameter. Since the tissue pieces being removed commonly have dimensions that are 1 to 2 lumen diameters in length, the tissue pieces can often clog the tissue removal lumen.

One portion of the body in which tissue can be removed to treat a variety of conditions is the spine area. Tissue removal devices for the spine are needed that can be produced with sufficiently small dimensions and/or that have increased performance over existing techniques. For example, a herniated disc or bulging disc can be treated by performing a discectomy, e.g. by removing all or part of the nucleus pulposus of the damaged disc. Such procedures may also involve a laminotomy or laminectomy wherein a portion or all of a lamina may be removed to allow access to the herniated disc. Artificial disc replacement (total or partial) is another example of a procedure which requires the removal of all or a portion of the disc, which is replaced with an artificial device or material.

Tissue removal devices are needed which can be produced with sufficient mechanical complexity and a small size so that they can both safely and more efficiently remove tissue from a subject, and/or remove tissue in a less invasive procedure and/or with less damage to adjacent tissue such that risks are lowered and recovery time is improved.

SUMMARY OF THE DISCLOSURE

According to some aspects of the disclosure, a medical device for removing tissue from a subject is provided. One exemplary device includes a distal housing, an elongate member, a first rotatable member and a second rotatable member. The distal housing is configured with at least one tissue engaging opening. The elongate member is coupled to the distal housing and configured to introduce the distal housing to a target tissue site of the subject. The first rotatable member is located at least partially within the distal housing and is configured to rotate about a first axis. The first rotatable member comprises a first disc-shaped blade having a series of teeth along an outer circumference of the blade. The first blade lies in a first plane. The first rotatable member further includes a circular first axle portion lying in a second plane that is offset from, parallel and adjacent to the first plane. The first axle portion has an outer circumference that is smaller than that of the first blade. The second rotatable member is also located at least partially within the distal housing and is configured to rotate about a second axis parallel to and offset from the first axis. The second rotatable member is configured to rotate in a direction opposite of a direction of rotation of the first rotatable member. The second rotatable member includes a second disc-shaped blade having a series of teeth along an outer circumference of the blade. The second blade lies in the second plane. The second rotatable member further includes a circular second axle portion lying in the first plane. The second axle portion has an outer circumference that is smaller than that of the second blade. The first and second blades are directly adjacent to one another and positioned to partially overlap such that tissue may be sheared between the first and second blades, between the first blade and the second axle portion and between the second blade and the first axle portion. The rotatable members are configured to engage tissue from the target tissue site with the teeth of the first and second blades, rotate towards one another and inwardly to direct tissue from the target tissue site through the tissue engaging opening and into an interior portion of the distal housing.

In some embodiments, the first rotatable member further includes a third disc-shaped blade having a series of teeth along an outer circumference of the blade. In these embodiments, the third blade lies in a third plane that is offset from, parallel and adjacent to the second plane. The second rotatable member further includes a circular third axle portion lying in the third plane. The third axle portion has an outer circumference that is smaller than that of the third blade. The second and third blades are directly adjacent to one another and positioned to partially overlap such that tissue may be sheared between the second and third blades and between the third blade and the third axle portion. The rotatable members are configured to engage tissue from the target tissue site with the teeth of the first, second and third blades, rotate towards one another and inwardly to direct tissue from the target tissue site through the tissue engaging opening and into an interior portion of the distal housing.

In some embodiments, the distal housing further includes a tissue cutting portion lying in a third plane that is offset from, parallel and adjacent to the second plane. In these embodiments, the tissue cutting portion and the second blade are directly adjacent to one another and positioned to partially overlap such that tissue may be sheared between the tissue cutting portion of the distal housing and the second blade.

In some embodiments, the first and second blades are no more than 30 microns apart where they partially overlap. In some embodiments, the outer circumference of the first blade is no more than 30 microns apart from the outer circumference of the second axle portion, and the outer circumference of the second blade is no more than 30 microns apart from the outer circumference of the first axle portion. The first and the second blades and the first and the second axle portions may each have a thickness of less than 1 mm. The first and the second rotation axes may be generally perpendicular to a longitudinal axis of the elongate member.

In some embodiments, the rotations of the first and the second rotatable members are synchronized such that a first trough associated with one of the teeth located along the outer circumference of the first blade and a second trough associated with one of the teeth located along the outer circumference of the second blade simultaneously engage a single fiber or single bundle of fibers from the target tissue site. In these embodiments, the first and the second troughs cooperate to compress portions of the single fiber or single bundle of fibers as the first and the second rotatable members rotate toward one another, thereby reducing the volume of the tissue entering the distal housing.

In some embodiments, the rotations of the first and the second rotatable members are configured to alternately rotate in and out of phase with one another. The first and the second rotatable members may be independently driven. The first and the second rotatable members may be configured to periodically reverse direction of rotation during tissue cutting, and may be configured to reverse direction at least once per second. The device may be configured to provide a dwell time of at least about 50 milliseconds when the first and the second rotatable members reverse direction.

According to aspects of the disclosure, methods of fabricated the above devices are disclosed. In some embodiments, the method includes fabricating the first blade and the second axle portion together in a first material deposition process step and fabricating the second blade and the first axle portion together in a second material deposition process step.

According to aspects of the disclosure, methods of using the above devices are disclosed. In some embodiments, the method includes urging the distal housing of the device against a target tissue site of a subject and extracting cut tissue pieces from a proximal end of the elongate member.

Other aspects of the disclosure will be understood by those of skill in the art upon review of the teachings herein. Other aspects of the disclosure may involve combinations of the above noted aspects of the disclosure. These other aspects of the disclosure may provide various combinations of the aspects presented above as well as provide other configurations, structures, functional relationships, and processes that have not been specifically set forth above.

BRIEF DESCRIPTION OF THE DRAWINGS

FIGS. 7A-7F show details of an exemplary rotor housing assembly 5420'.

DETAILED DESCRIPTION

Figure 1:
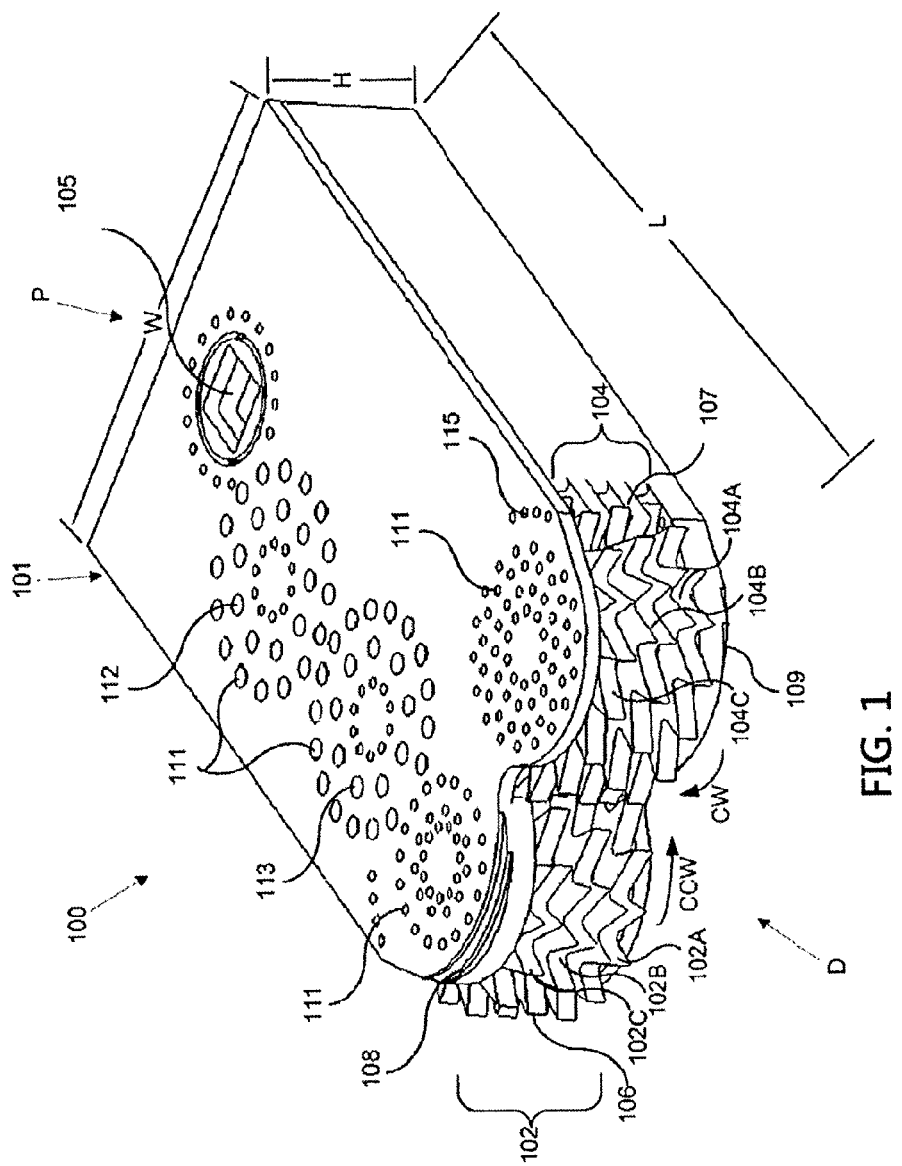
FIGS. 1-3 illustrate an exemplary embodiment of a working end of a tissue removal device.
Figure 2:
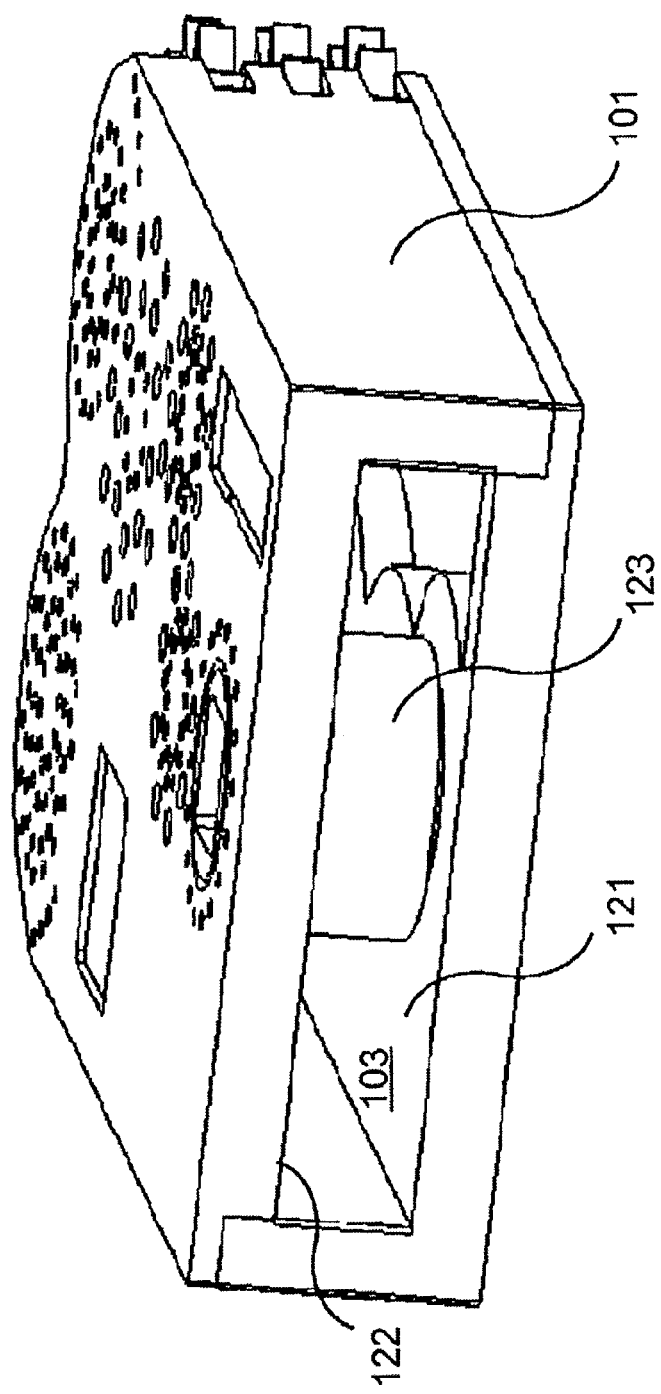
Figure 3:
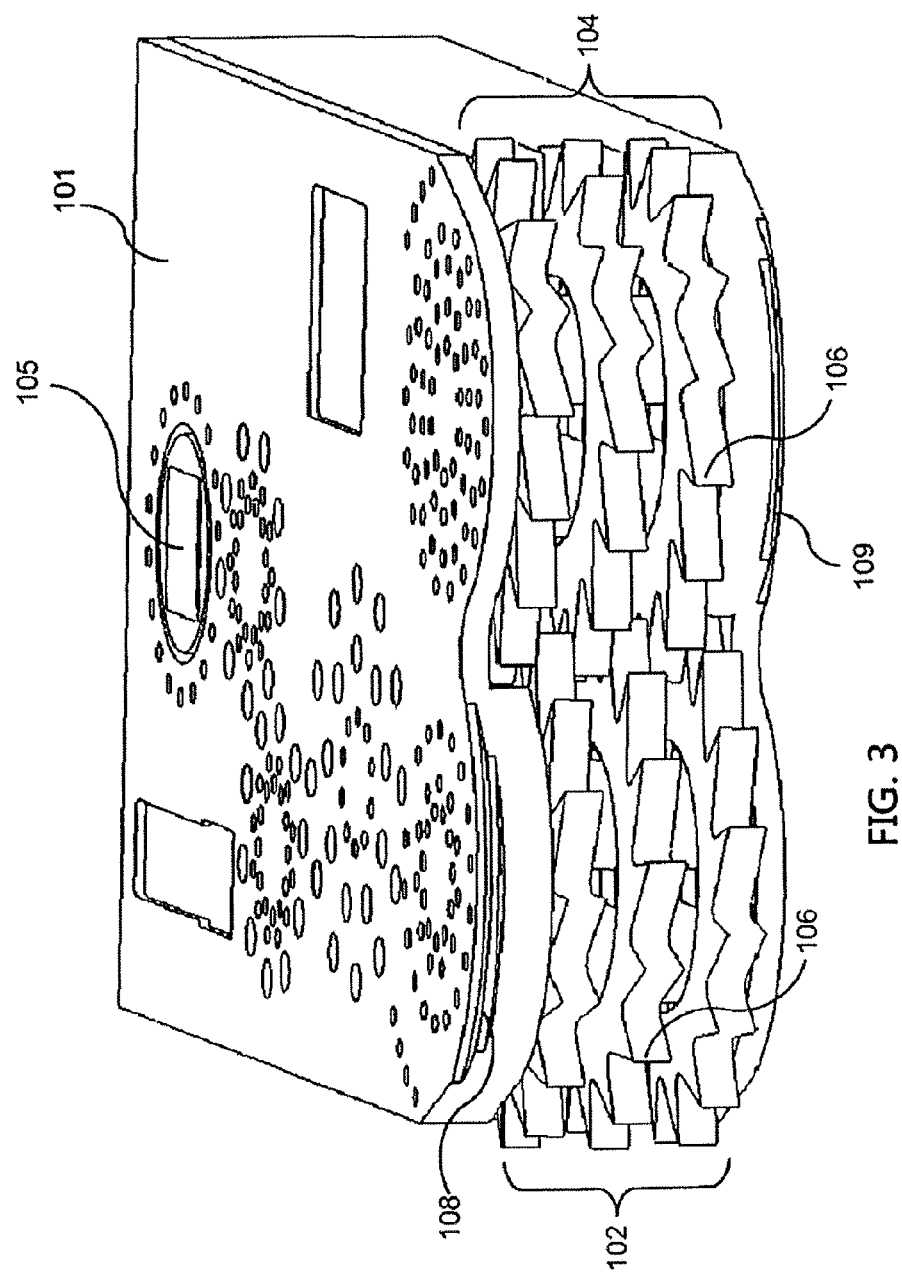

FIGS. 1-3 illustrate an exemplary embodiment of a working end of a tissue removal device, which can be fabricated wholly or in part by electrochemical fabrication techniques, such as those described or referenced herein. Tissue removal device working end 100 has a distal region "D" and proximal region "P," and includes housing 101 and blade stacks 102 and 104. Blade stacks 102 and 104 include a plurality of blades 102A-102C and 104A-104C, respectively. Three blades are shown in each stack, although the blade stacks can have one or more blades. Each of the blades includes a plurality of teeth 106 (see FIG. 3), some of which are shown projecting from housing 101 and configured to engage and process tissue. Processing tissue as used herein includes any of cutting tissue, shredding tissue, capturing tissue, any other manipulation of tissue as described herein, or any combination thereof. The working end of the device generally has a length L, height H, and width W. Housing 101 can have a variety of shapes or configurations, including a generally cylindrical shape.

In this embodiment both blade stacks are configured to rotate. The blades in blade stack 102 are configured to rotate in a direction opposite that of the blades in blade stack 104, as designated by the counterclockwise "CCW" and clockwise "CW" directions in FIG. 1. The oppositely rotating blades direct material, such as tissue, into an interior region of housing 101 (described in more detail below). In some embodiments, the blades can be made to be rotated in directions opposite to those indicated, e.g. to disengage from tissue if a jam occurs or to cause the device to be pulled distally into a body of tissue when given appropriate back side teeth configurations.

Housing 101 also includes a drive mechanism coupler 105, shown as a square hole or bore, which couples a drive train disposed in the housing to a drive mechanism disposed external to the housing. The drive mechanism, described in more detail below, drives the rotation of the drive train, which drives the rotation of the blades. The drive train disposed in the housing can also be considered part of the drive mechanism when viewed from the perspective of the blades. Drive mechanism coupler 105 translates a rotational force applied to the coupler by the drive mechanism (not shown) to the drive train disposed within housing 101.

FIG. 1 also shows release holes 111-115 which allow for removal of sacrificed material during formation of the working end.

FIG. 2 shows a perspective view of the proximal end of tissue removal device working end 100. Material directed into housing 101 by the rotating blades is directed into chamber 103, wherein it can be stored temporarily or directed further proximally, as described below. A first gear train cover 121 provides for a first surface of chamber 103, while a second gear train cover 122 provides a second surface of chamber 103. FIG. 2 also shows drive mechanism coupler cover 123.

In some embodiments in which the working end 100 includes a storage chamber, the chamber may remain open while in other embodiments it may be closed while in still other embodiments it may include a filter that only allows passage of items of a sufficiently small size to exit.

FIG. 3 shows a perspective view of the distal end of the working end 100. In this embodiment the blades in stack 102 are interdigitated with the blades in stack 104 (i.e. the blade ends are offset vertically along dimension H and have maximum radial extensions that overlap laterally along the width dimension W. The blades can be formed to be interdigitated by, e.g. if formed using a multi-layer, multi-material electrochemical fabrication technique, forming each blade in stack 102 in a different layer than each blade in stack 104. If during formation portions of separately moveable blade components overlap laterally, the overlapping blades should not just be formed on different layers but should be formed such an intermediate layer defines a vertical gap between them. For example, the bottom blade in stack 102 is shown formed in a layer beneath the layer in which the bottom blade in stack 104 is formed.

When manufacturing tissue removal devices of the various embodiments set forth herein using a multi-layer multi-material electrochemical fabrication process, it is generally beneficial if not necessary to maintain horizontal spacing of component features and widths of component dimensions remain above the minimum feature size. It is important that vertical gaps of appropriate size be formed between separately movable components that overlap in X-Y space (assuming the layers during formation are being stacked along the Z axis) so that they do not inadvertently bond together and to ensure that adequate pathways are provided to allow etching of sacrificial material to occur. For example, it is generally important that gaps exist between a gear element (e.g. a tooth) in a first gear tier and a second gear tier so that the overlapping teeth of adjacent gears do not bond together. It is also generally important to form gaps between components that move relative to one another (e.g., gears and gear covers, between blades and housing, etc.). In some embodiments the gaps formed between moving layers is between about 2 um and about 8 um.

In some embodiments, it is desired to define a shearing thickness as the gap between elements has they move past one another. Such gaps may be defined by layer thickness increments or multiples of such increments or by the intra-layer spacing of elements as they move past one another. In some embodiments, shearing thickness of blades passing blades or blades moving past interdigitated fingers, or the like may be optimally set in the range of 2-100 microns or some other amount depending on the viscosity or other parameters of the materials being encountered and what the interaction is to be (e.g. tearing, shredding, transporting, or the like). For example for shredding or tearing tissue, the gap may be in the range of 2-10 microns, or in some embodiments in the range of 4-6 microns.

Figure 4A:
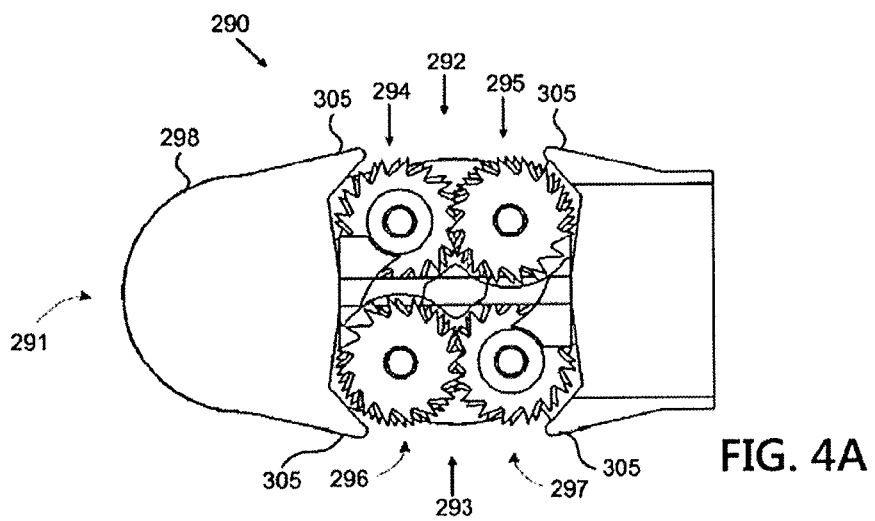
FIGS. 4A-4G illustrate exemplary embodiments of drive mechanisms which can power the drive trains in the working end of tissue removal devices.
Figure 4B:
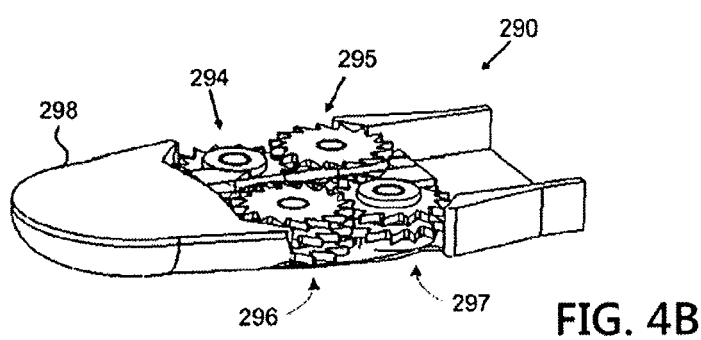
Figure 4C:
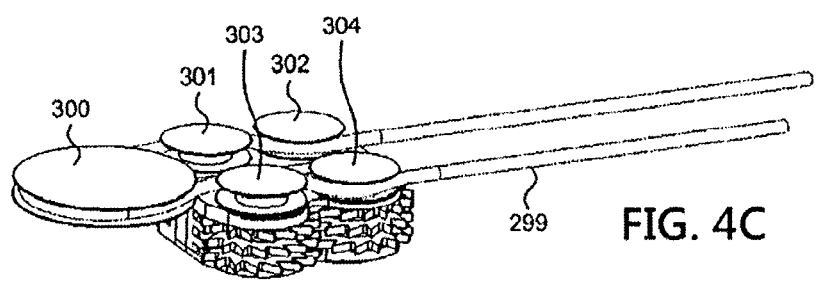
Figure 4D:
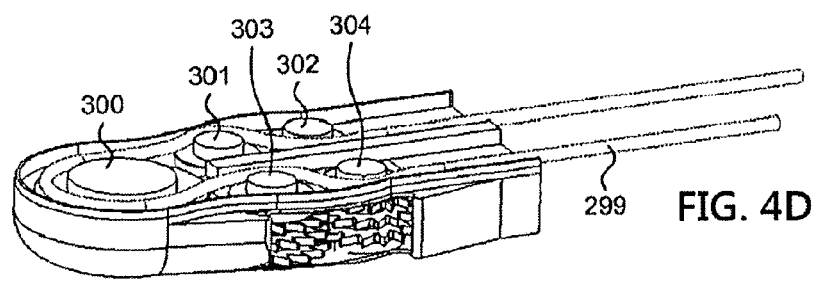
Figure 4E:
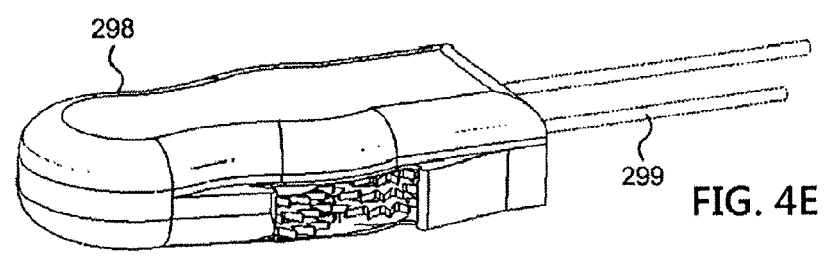
Figure 4F:
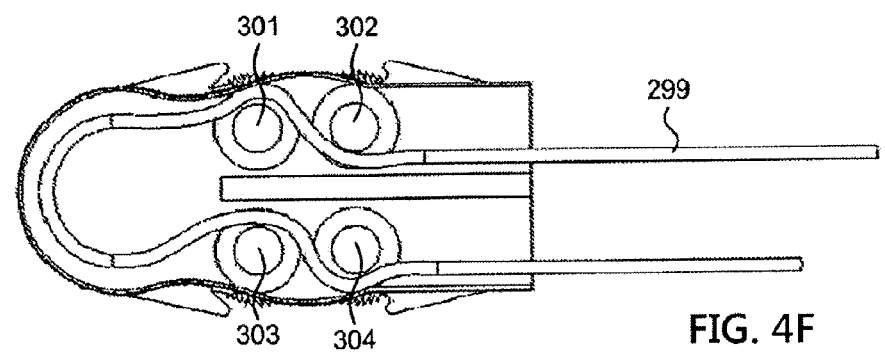
Figure 4G:
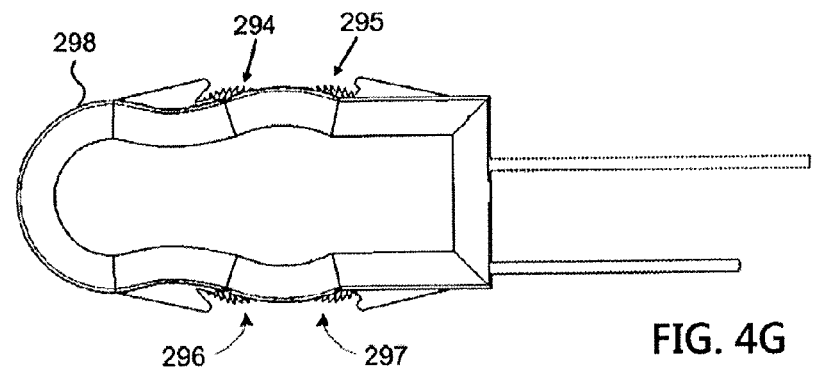

FIGS. 4A-4G illustrate an example a of a side tissue removal working end. FIG. 4A is a top sectional view with a top portion of the housing removed, which shows working end 290 comprising housing 298 and four tissue removal elements 294-297, which are shown as blade stacks. Blade stacks 294 and 295 process tissue along one side of the housing by directing tissue in the direction of arrow 292. Blade stacks 296 and 297 process tissue along a second side of the housing by directing tissue in the direction of arrow 293. As shown in FIGS. 4A-B, blade stacks 294 and 297 each have two blades, while blade stacks 295 and 296 each have three blades. FIG. 4C shows a perspective view without housing 298 illustrating the drive mechanism for the side tissue removal device 290. The drive mechanism includes belt 299, distal pulley 300, and side pulleys 301-304. The side pulleys are coupled to the blade stacks and rotation of the side pulleys rotates the blade stacks. The belt is disposed through side pulleys 301 and 302 and around distal pulley 300 before returning through side pulleys 303 and 304. Actuating of belt 299 therefore activates all four blade stacks. In some embodiments the belt is a nitinol wire, but can be any other suitable material. FIG. 4D is a view with the top portion of the housing removed to show the internal drive mechanism. FIG. 4E shows the same view with the top on the housing. FIGS. 4F and 4G show top views of the working end shown in FIGS. 4D and 4E, respectively. Vacuum, irrigation, or a combination of the two may be used to send extracted tissue from the interior of the working end, proximally to a storage reservoir (e.g. within the working end or located outside the body of the patient on which a procedure is being performed).

Figure 5A:
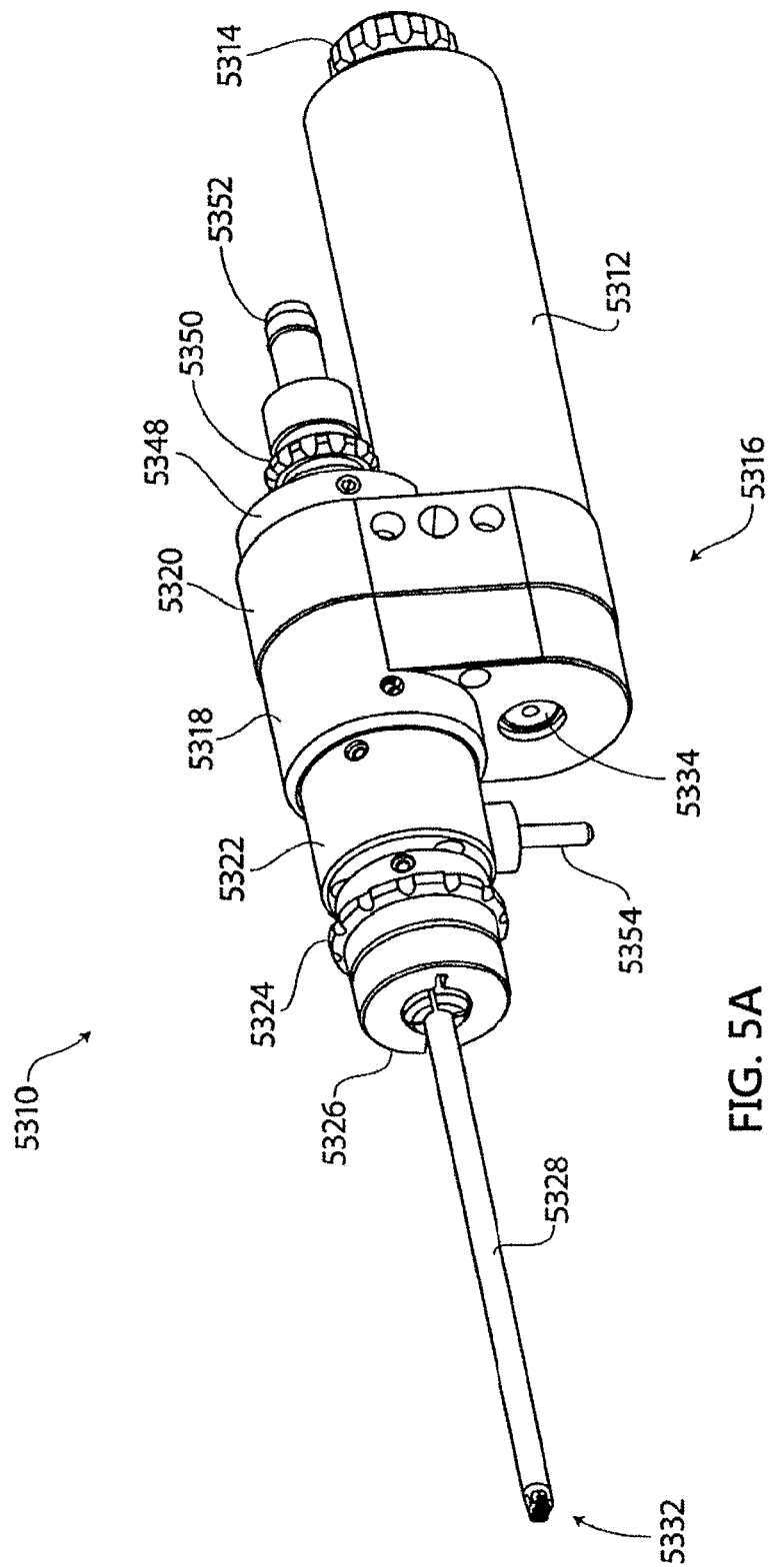
FIGS. 5A-5C show another exemplary embodiment of a tissue removal device.
Figure 5B:
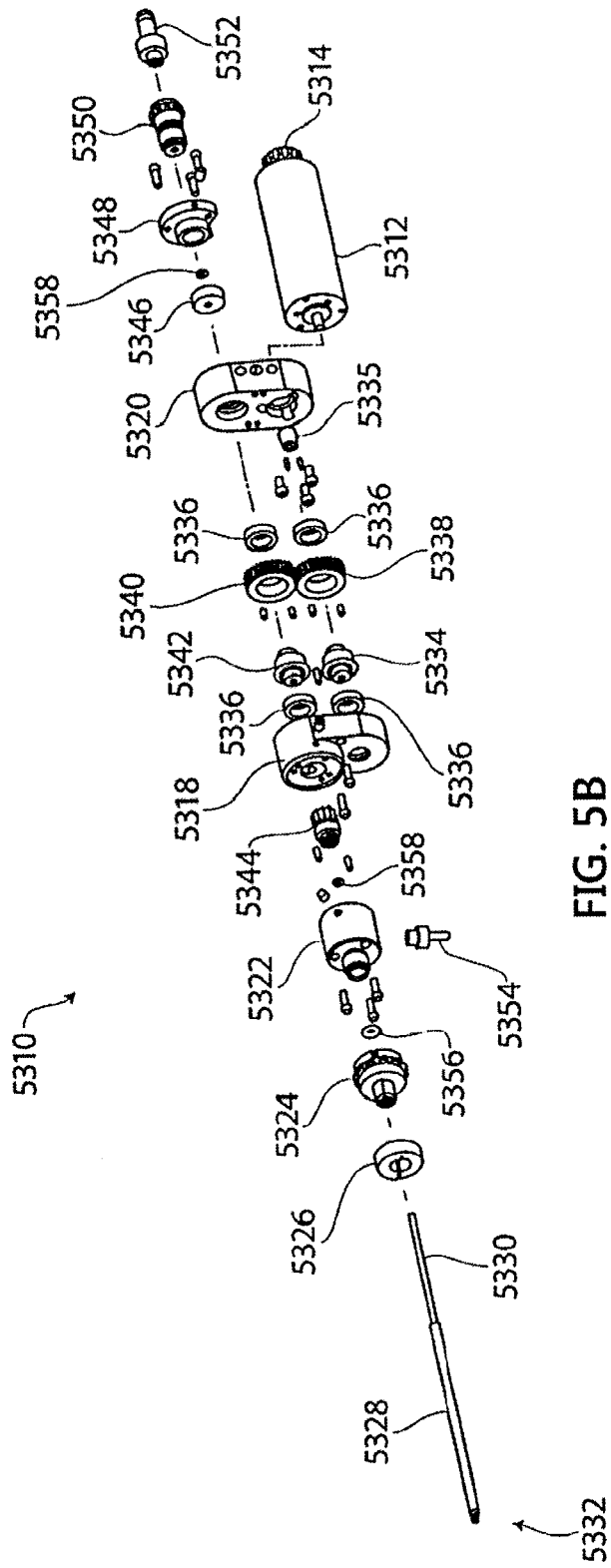
Figure 5C:
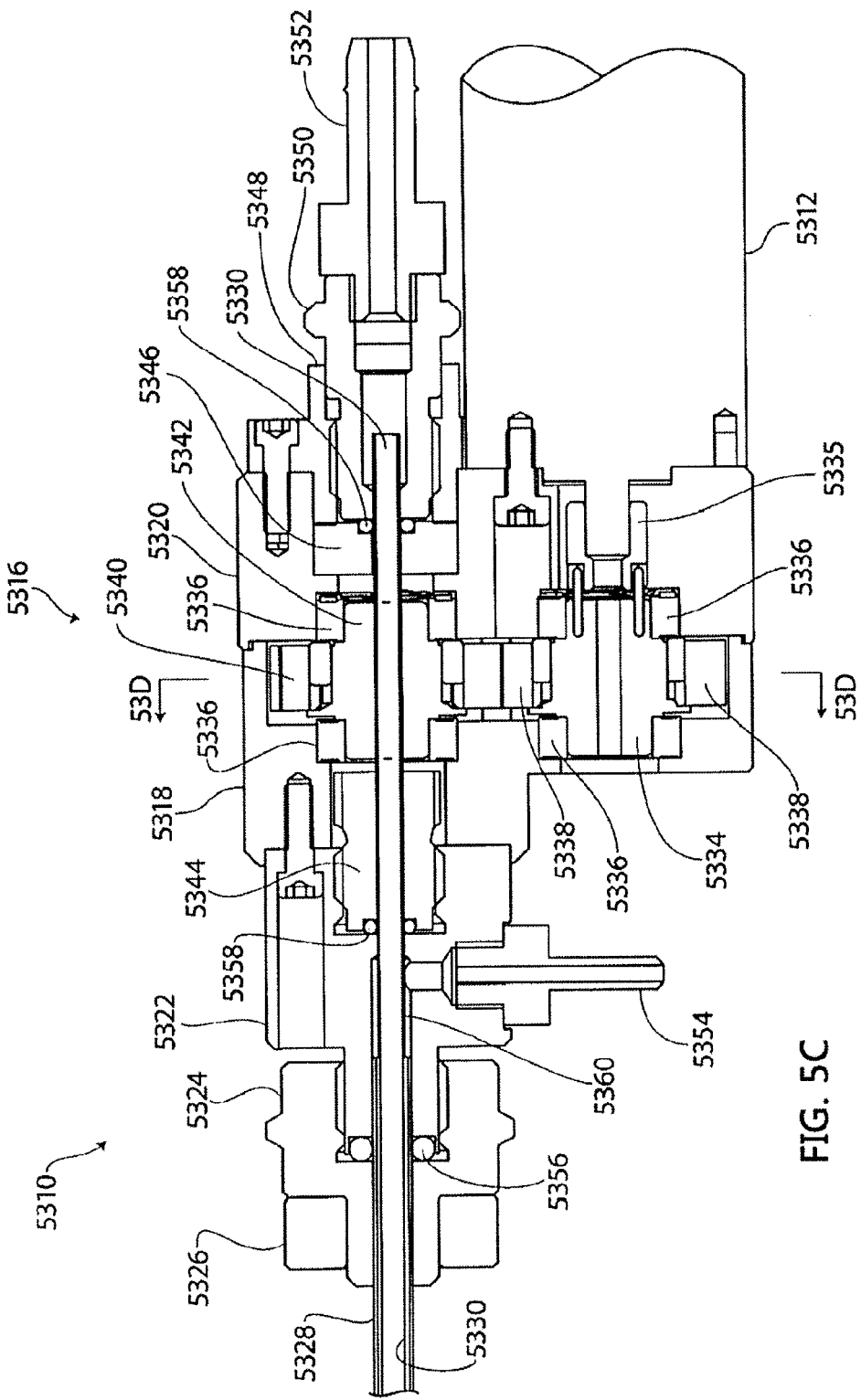

FIGS. 5A-5C show another exemplary embodiment of a tissue removal device. Device 5310 may employ any of the cutting heads described herein, or other suitable cutting heads. In some embodiments, a double rotor shredding head is employed at the distal end of device 5310 to selectively debride tissue down to the cellular level.

In this exemplary embodiment, handheld device 5310 includes a stepper motor 5312 at its proximal end. In other embodiments, other types of electric, pneumatic or hydraulic motors, servos, or other prime movers may be used. The proximal end of motor 5312 may be provided with a manually turnable thumbwheel 5314, as shown. In this embodiment, the distal output end of motor 5312 is provided with a housing 5316, which is made up of a front cover 5318 and a rear cover 5320. Located distally from housing 5316 are an outer shaft housing 5322, an outer shaft lock seal 5324, and a support clamp 5326. A non-rotating, outer support tube 5328 extends from within the proximal end of device 5310 towards the distal end of the device. Within support tube 5328, a rotating drive tube 5330 (best seen in FIGS. 5B and 5C) also extends from within the proximal end of device 5310 towards the distal end of the device. The support tube 5328 and inner drive tube 5330 may collectively be referred to as an introducer. A cutter head assembly 5332, subsequently described in detail, is attached to the distal end of support tube 5328.

As best seen in FIG. 5B, other components of device 5310 include motor shaft drive axle 5334, motor dog 5335, four bearings 5336, drive gear 5338, driven gear 5340, inner drive shaft axle 5342, inner shaft lock seal 5344, vacuum gland disk 5346, vacuum seal lock housing 5348, vacuum seal lock 5350, vacuum hose barb 5352, irrigation fluid hose barb 5354, outer tube o-ring 5356, and two vacuum gland o-rings 5358. Various other pins, dowels, fasteners, set screws, ball detents, shims and wave disc springs are shown in the figures without reference numerals. As will be appreciated by those skilled in this art, these non-referenced components serve to align, retain and ensure the proper functioning of the other components of exemplary device 5310.

The two rotors of cutter head assembly 5332 located at the distal end of device 5310 are driven by motor 5312 through drive tube 5330 and other drive components of device 5310, as will now be described in more detail. As best seen in FIGS. 5B and 5C, a motor dog 5335 is attached to the output shaft of motor 5312. Motor dog 5335 is coupled to motor shaft drive axle 5334, which is rotatably mounted in housing 5316 with two bearings 5336. Drive gear 5338 is rigidly fixed to motor shaft drive axle 5334, and drives driven gear 5340. Driven gear 5340 is rigidly fixed to inner drive shaft axle 5342, which is rotatably mounted in housing 5316 with two bearings 5336. Inner rotating drive tube 5330 passes through the center of inner drive shaft axle 5342 and is rotatably fixed thereto. Drive tube 5330 extends from the proximal end of device 5310 to the distal end of the device through the non-rotating outer support tube 5328. The distal end of drive tube 5330 (or a separate tube 5330' attached thereto) is provided with crown teeth around its periphery, as shown in FIGS. 6B and 6C, for meshing with drive gear 5410. As drive tube 5330 is rotated about a longitudinal axis of device 5310 by motor 5312 through the above-described drive train components, it drives drive gear 5410 about an axis that is perpendicular to the longitudinal axis, as can be appreciated by viewing FIG. 6. Drive gear 5410 in turn drives other components of the cutter head assembly, and as is subsequently described in more detail.

In some embodiments motor 5312 is provided with feedback control for rotational velocity and torque. These two parameters can be used for controlling and monitoring changes in rotational velocity and the torque load. For measuring rotational velocity, an encoder may be located at one or more of the cutter rotors, at the drive motor, or at another location along the drive train between the drive motor and cutter rotors. In some embodiments, the encoder is located at or close to the rotors to avoid backlash associated with the drive train, thereby making the velocity monitoring more responsive and accurate. Encoder technologies that may be used include optical, resistive, capacitive and/or inductive measurement. To sense torque load, one or more strain gages may be located at the cutter rotors, at the drive motor, or at another location along the drive train between the drive motor and cutter rotors. Torque load may also be sensed by monitoring the current being drawn by the motor. By sensing changes in velocity and/or torque, a controller associated with device 5310 can determine that the cutter rotors are passing from one tissue type to another and take appropriate action. For example, the controller can sense when the cutter elements are passing from soft to hard tissue, from hard to medium density tissue, or from a cutting state to non-cutting state. In response to these changes, the controller and/or device 5310 can provide audio, visual and/or tactile feedback to the surgeon. In some embodiments, the controller can change the velocity, direction or stop cutter rotors from rotating in response to velocity and/or torque feedback. In one embodiment of the invention, a typical cutting rotor speed is on the order of 100 to 20,000 rotations per minute, and a typical torque load is on the order of 0.25 to 150 mN-meter. Other sensors, such as a pressure sensor or strain sensor located at the distal tip of device 5310, may also be utilized to provide feedback that tissue cutting elements are moving from one tissue type to another. In some embodiments, an impendence sensor may be located at the distal tip of the device, to sense different tissue types or conditions, and provide corresponding feedback for tissue cutting control when the tissue being cut by the cutter head changes. Such a pressure sensor feedback control arrangement can be used with types of cutting devices other than those disclosed herein.

Referring now to FIG. 5C, irrigation fluid hose barb 5354 is provided on the lower side of outer shaft housing 5322 of exemplary device 5310. Hose barb 5354, or a similar fluid line coupling, may be connected to a supply of irrigation fluid. The lumen of hose barb 5354 is in fluid communication with an internal irrigation fluid cavity 5360. Fluid cavity 5360 surrounds internal drive tube 5330, and is bounded on its proximal end by o-ring seal 5358 around drive tube 5330. Fluid cavity 5360 is bounded on its distal end by o-ring seal 5356 around outer support tube 5328. This arrangement allows drive tube 5330 to rotate, but constrains irrigation fluid delivered from hose barb 5354 to travel only through the annular space defined by the outer surface of drive tube 5330 and the inner surface of support tube 5328. Irrigation fluid may thus flow distally through the annular space to the distal end of device 5310.

As shown in FIG. 6B, one or more drive aligner rings 5412 may be provided between outer support tube 5328 and inner drive tube 5330 along their lengths to support drive tube 5330 as it rotates. In order to allow the flow of irrigation fluid between the tubes 5328 and 5330, rings 5412 may be provided with one or more channels 5414 as shown. When the distal flow of irrigation fluid reaches the cutter head assembly 5332, it continues to flow distally into lug 5416. To enable the fluid flow, lug 5416 is provided with fluid channels 5418 located along the outer walls of its central bore, as best seen in FIG. 6C. In this embodiments, irrigation fluid passes distally between inner drive tube 5330 and lug 5416 through channels 5418 (only one channel shown in FIG. 6C). Irrigation fluid flowing distally through channels 5418 may be directed toward the outside portions of cutting elements. In this embodiment, the outside portions of cutting elements are rotating distally, away from the fluid flow, while the inside portions of cutting elements are rotating proximally, toward the center of lug 5416 and drive tube 5330.

In some embodiments, the irrigation fluid serves multiple functions. The irrigation fluid can serve to lubricate the cutting elements, drive gears, journal bearings and other components as the parts rotate. The irrigation fluid can also serve to cool the cutting elements and/or the tissue being cut, absorbing heat and carrying it away as the irrigation fluid is removed from the patient. The fluid can serve to flush tissue particles from the moving parts to prevent them from becoming clogged. The fluid can also serve to carry away the tissue portions being cut and remove them from the target tissue site. In some embodiments, the irrigation fluid is discharged from the cutting device and may be removed from the target tissue site with other, traditional aspiration means. With the current exemplary cutting device 5310, however, the irrigation fluid and/or other bodily fluids may be removed from the target tissue site by the cutting device 5310, as will now be described in detail.

As previously described, irrigation fluid may be delivered to cutting elements and/or a target tissue site through device 5310. Exemplary device 5310 is also constructed to remove the irrigation fluid and tissue portions cut from the target tissue site through the shaft of device 5310. As can be appreciated by viewing FIG. 7F, the two interleaving stacks of cutting elements, also referred to as rotors 5610 and 5612, have an overlapping section 5614 in the center of cutter head assembly 5332. The two rotors 5610 and 5612 may be rotated in opposite directions such that each rotor engages target tissue and pulls it towards the central overlapping section 5614. In overlapping section 5614, the tissue is shredded into small pieces by the interdigitated cutting elements, as is subsequently described in more detail. The small tissue portions are generally propelled in a proximal direction by rotors 5610 and 5612, away from the target tissue site and into the cutter head assembly 5332. As can be appreciated by viewing FIG. 7F, the shredded tissue portions emerge from rotors 5610 and 5612 substantially along the central axis of lug 5416 (and therefore also the central axis of drive tube 5330. With sufficient irrigation fluid being supplied to the tissue cutting area, and sufficient aspiration being provided from the proximal end of the device, irrigation fluid around rotors 5610 and 5612 carries the cut tissue particles proximally down the center of drive tube 5330. As shown in FIG. 5C, the proximal end of drive tube 5330 is in fluid communication with hose barb 5352 located at the proximal end of device 5310. A traditional aspiration device or other suction source may be attached to device 5310 through hose barb 5352 or other suitable fluid coupling to collect the spent irrigation fluid and cut tissue portions.

In some embodiments, the cut tissues portions emerging from hose barb 5352 may be collected for testing. The tissue portions may be separated from the irrigation fluid, such as by centrifugal force, settling and/or filtering. The tissue portions may be measured to precisely determine the mass and/or volume of tissue removed. The pathology of some or all of the tissue portions may also be determined. In some embodiments, the above testing may be performed during a surgical procedure so that results of the testing may be used to affect additional stages of the procedure.

According to aspects of the invention, the inside diameter of drive tube 5330 may be much larger than the maximum dimension of the tissue portions traveling through it. In some embodiments, the maximum tissue dimension is less than about 2 mm across. In one exemplary embodiment, the inside diameter of drive tube 5330 is about 3 mm, the outside diameter of the support tube 5328 is about 5.6 mm, and the maximum dimension of the tissue portions is about 150 microns. In another exemplary embodiment, the inside diameter of drive tube 5330 is about 1.5 mm, the outside diameter of the support tube 5328 is about 2.8 mm, and the maximum dimension of the tissue portions is about 75 microns. In other embodiments, the inside diameter of drive tube 5330 is between about 3 mm and about 6 mm. In some embodiments, the maximum dimension of the tissue portions is at least one order of magnitude less than a diameter of the tissue removal lumen. In other embodiments, the maximum dimension of the tissue portions is at least twenty times less than a diameter of the tissue removal lumen. In some embodiments, the maximum dimension of the tissue portions is less than about 100 microns. In other embodiments, the maximum dimension of the tissue portions is about 2 microns.

Figure 6A:
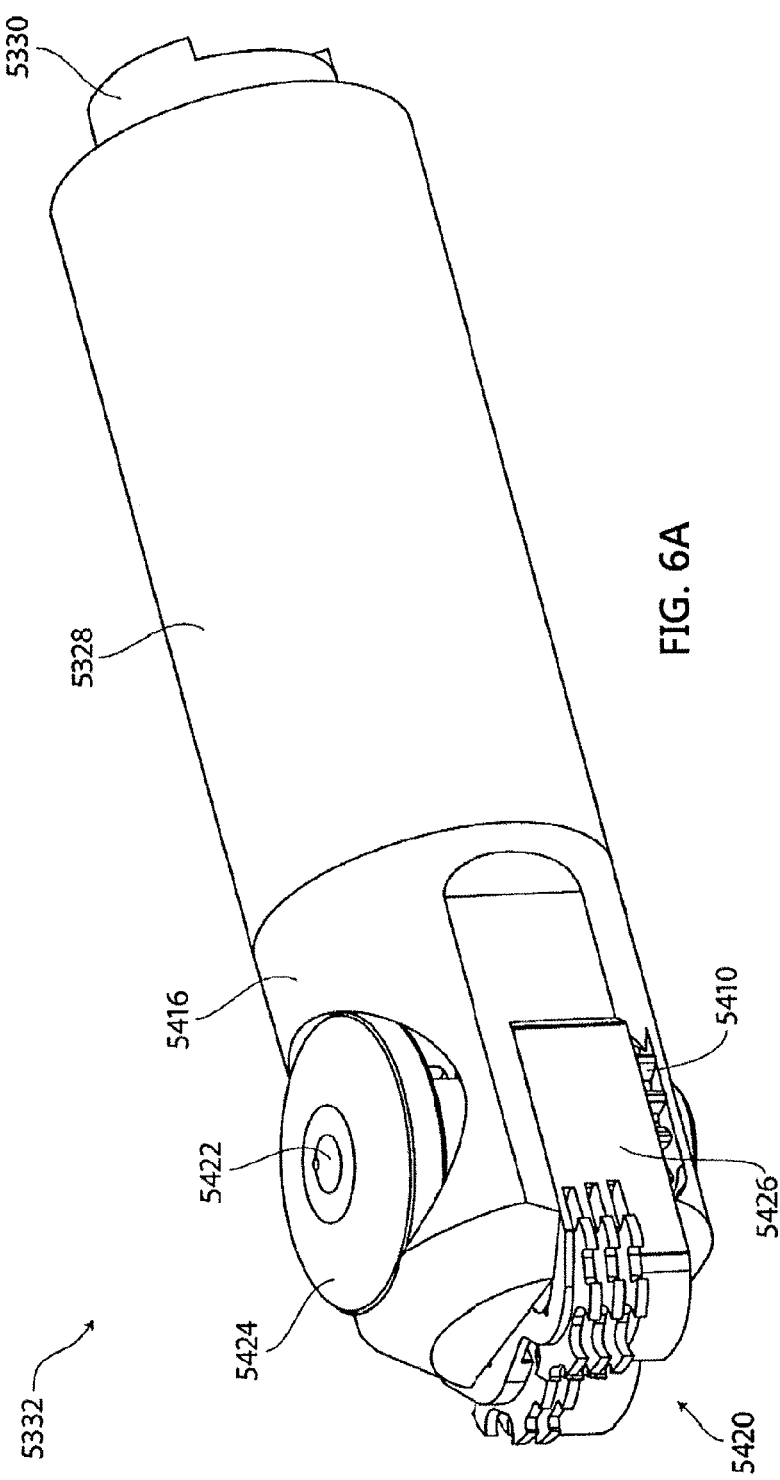
FIGS. 6A-6C show an exemplary cutter head assembly 5332 that may be used with debriding device 5310, shown in FIGS. 5A-5C.
Figure 6B:
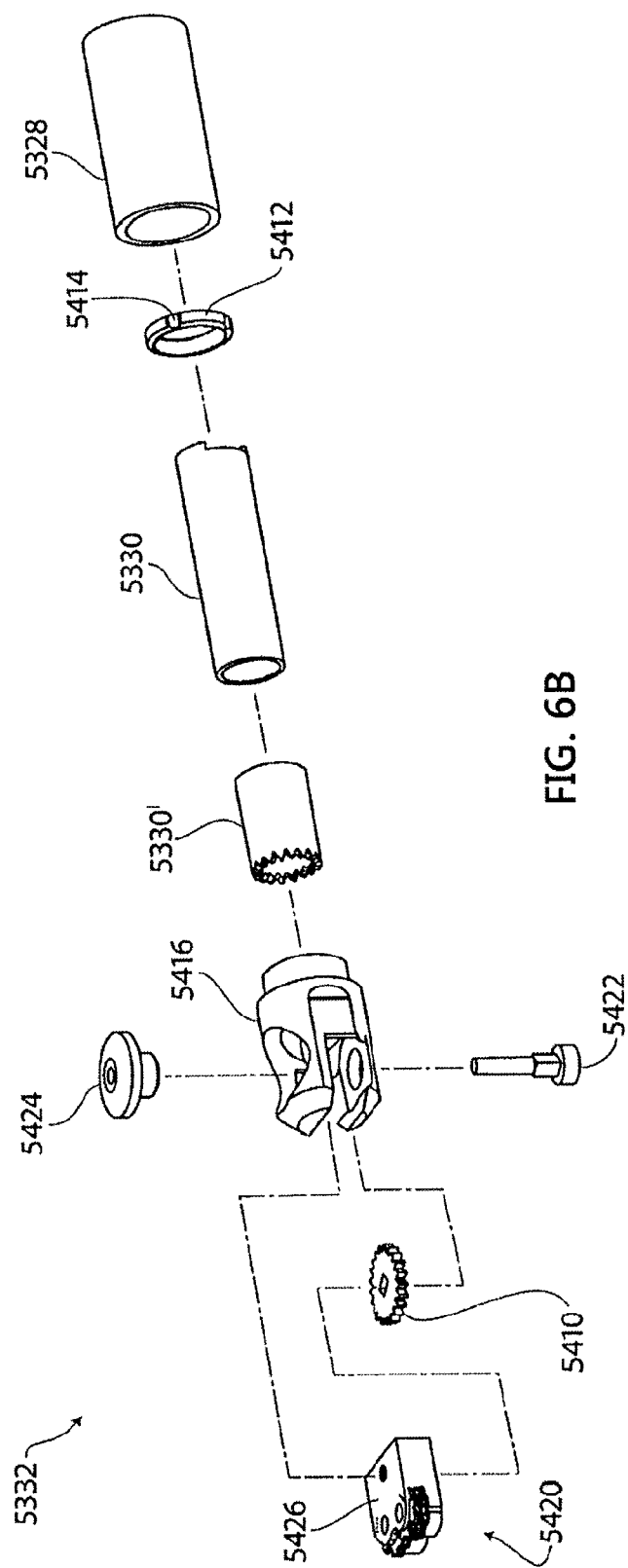
Figure 6C:
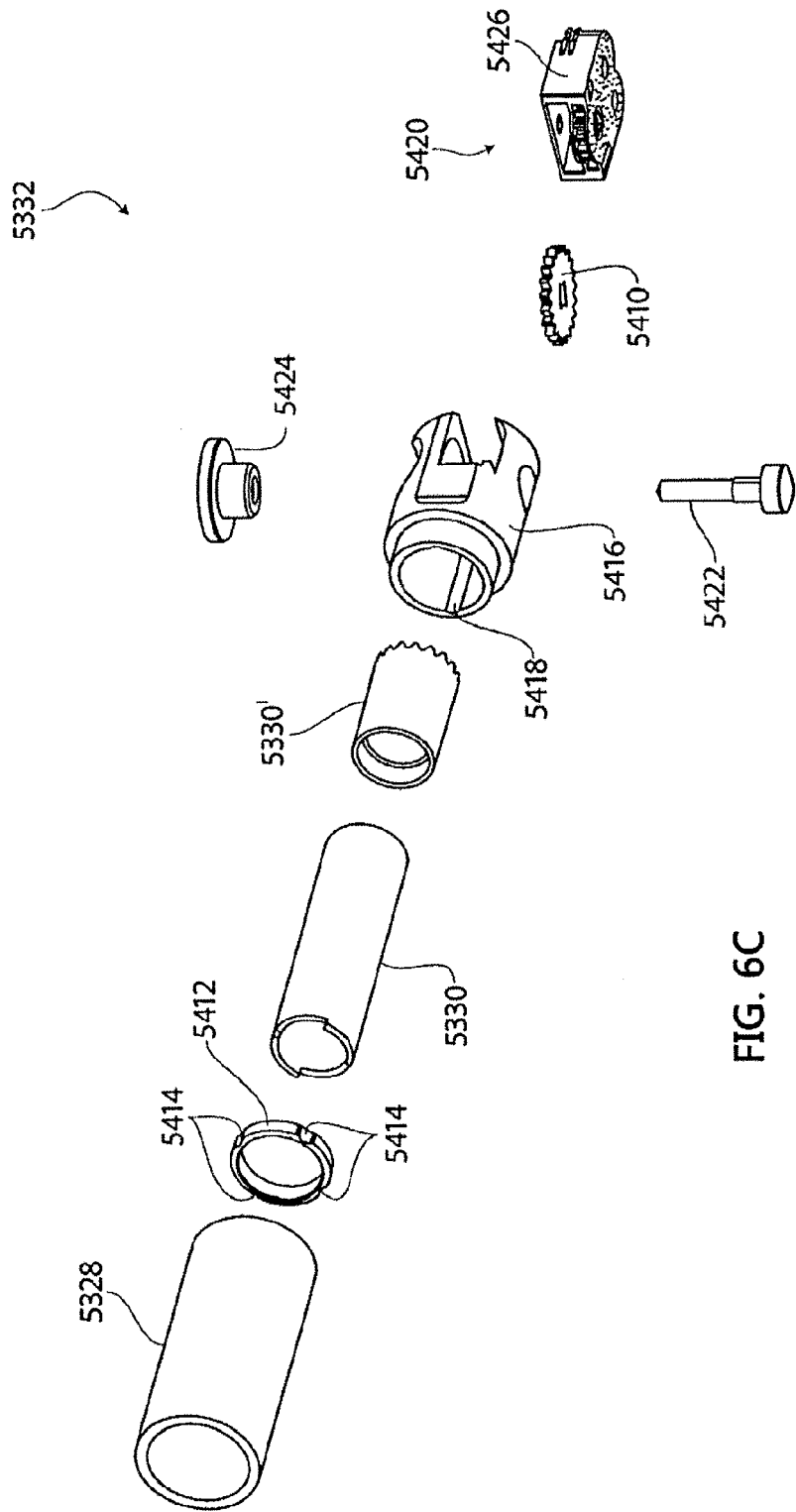

Referring now to FIGS. 6A-6C, an exemplary cutter head assembly 5332 is described in more detail. Cutter head assembly 5332 may be used with debriding device 5310, shown in FIGS. 6A-6C. As best seen in FIG. 6B, cutter head assembly 5332 includes lug 5416, drive gear 5410, rotor housing assembly 5420, aligner pin 5422, and aligner cap 5424. Lug 5416 is provided with a cutout on its distal end for receiving rotor housing assembly 5420. Beneath the rotor housing cutout, lug 5416 has a circular recess for receiving drive gear 5410. A bore is provided in the bottom of lug 5416 for receiving the head of aligner pin 5422. When cutter head 5332 is assembled, the shank of aligner pin 5422 passes through the bore of lug 5416, through a square aperture in the center of drive gear 5410, through a bore in the proximal end of rotor housing assembly 5420, and into a large diameter bore through the top of lug 5416. Aligner cap 5424 is received with the large diameter bore in the top of lug 5416, and is fastened to aligner pin 5422 by a press fit, weld, threads, a separate fastener, or other suitable means. In this assembled arrangement, pin 5422 and cap 5424 retain rotor housing 5426 from moving longitudinally relative to the central axis of the instrument, and rotor housing 5426 and drive gear 5410 retain pin 5422 and cap 5424 from moving radially relative to the central axis of the instrument. Pin 5422 and cap 5424 spin together as a unit relative to lug 5416, and serve to align drive gear with the distal end of drive tube 5330', as previously described. Pin 5422 also serves to transmit torque from drive gear 5410 to gear 5616, which resides inside the rotor housing directly above drive gear 5410. Lug bearing 5416 forms the base of cutter head assembly 5332, shown in FIGS. 6A-6C. As subsequently described in further detail, various different cutter heads may alternately be inserted into and secured within the slot shaped opening in the distal end of the lug bearing.

Figure 7A:
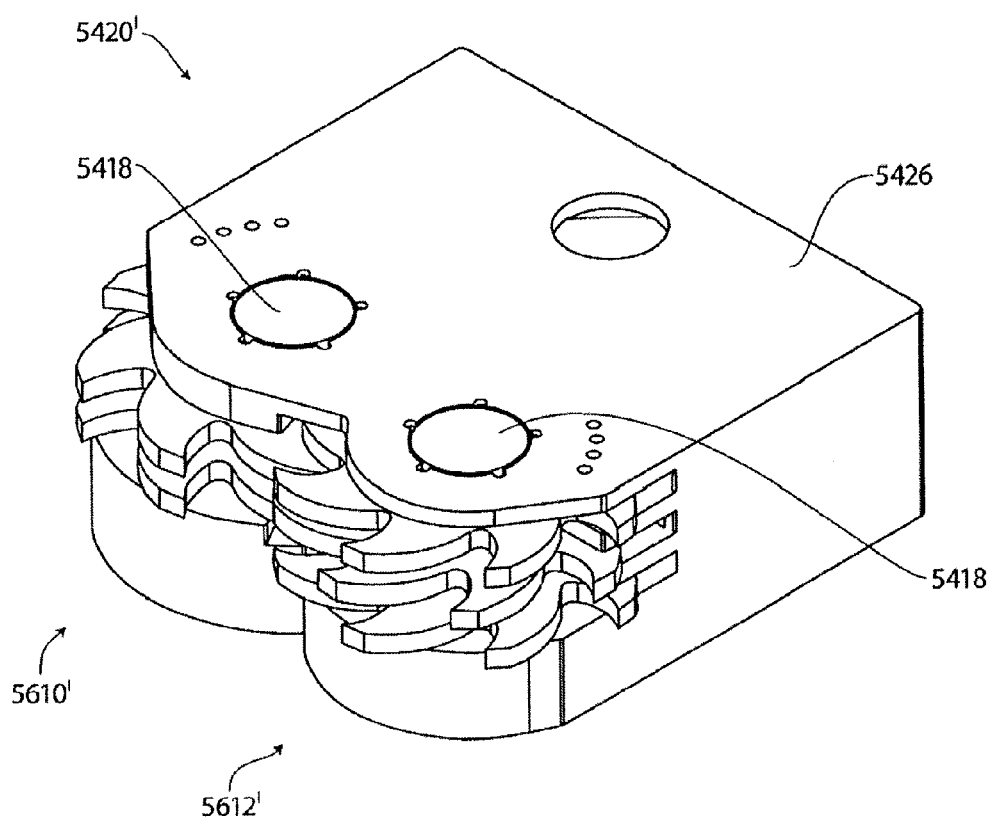

FIGS. 7A-7F show further details of an exemplary rotor housing assembly 5420'. Assembly 5420' is constructed and operates in a manner similar to assembly 5420 as previously described in reference to FIGS. 6A-6C, but has a different blade configuration. As shown in FIG. 7A, rotor housing assembly 5420' includes a pair of rotors 5610' and 5612', each rotatably mounted in rotor housing 5426 by an axle 5618. In this embodiment, rotors 5610' and 5612' are configured to rotate in opposite directions to draw tissue into a center, overlapping region where the tissue is shredded.

Referring to FIGS. 7B and 7C, the components of rotor housing assembly 5420' are shown. Assembly 5420' includes housing 5426, a pair of axles 5418, and gears 5410, 5620 and 5622, as previously described. Rotor 5610' includes two blades 5710 interspersed with three spacer rings 5714 on first axle 5418. Rotor 5612' includes three blades 5712 interspersed with two spacer rings 5716 on second axle 5418.

It should be noted that while rotor housing assembly 5420' is shown in an exploded format for clarity in FIGS. 7B and 7C, suggesting that the components are fabricated separately and then assembled using traditional assembly processes, this may or may not be the case, depending on the embodiment. In some embodiments, rotor assembly 5420' is assembled this way. In other embodiments, assembly 5420' may be built in layers, such as by using a MEMS fabrication processes. For example, after portions of housing 5426 and gears 5410, 5620 and 5622 are built up in layers, bottom blade 5712, bottom spacer 5714, and housing fin 5624 are formed together in one or more layers. Following this layer, bottom blade 5710, bottom spacer 5716, and bottom housing fin 5626 may be formed together in one or more layers. The process may be repeated until the entire rotors 5610' and 5612' and surrounding components are formed. A thin sacrificial layer may be formed between adjacent layers of components to separate the components from one layer from components of adjacent layers. Sacrificial material may also be formed in portions of each non-sacrificial layer to separate components on that layer, create desired voids in the finished assembly, and to provide a substrate for forming components in subsequent layers above. With such a fabrication technique, rotor 5610' may be formed as a single unitary structure interleaved with portions of rotor housing 5426, rather than separate components (i.e. axle 5418, spacers 5714, blades 5710, and gear 5620.) Similarly, rotor 5612' may be formed as a single unitary structure interleaved with portions of rotor housing 5426, rather than separate components (i.e. axle 5418, blades 5712, spacers 5716, and gear 5622.) In some embodiments, combinations of fabrication and assembly techniques may be used to create the rotor housing and/or cutter head assemblies.

Figure 7D:
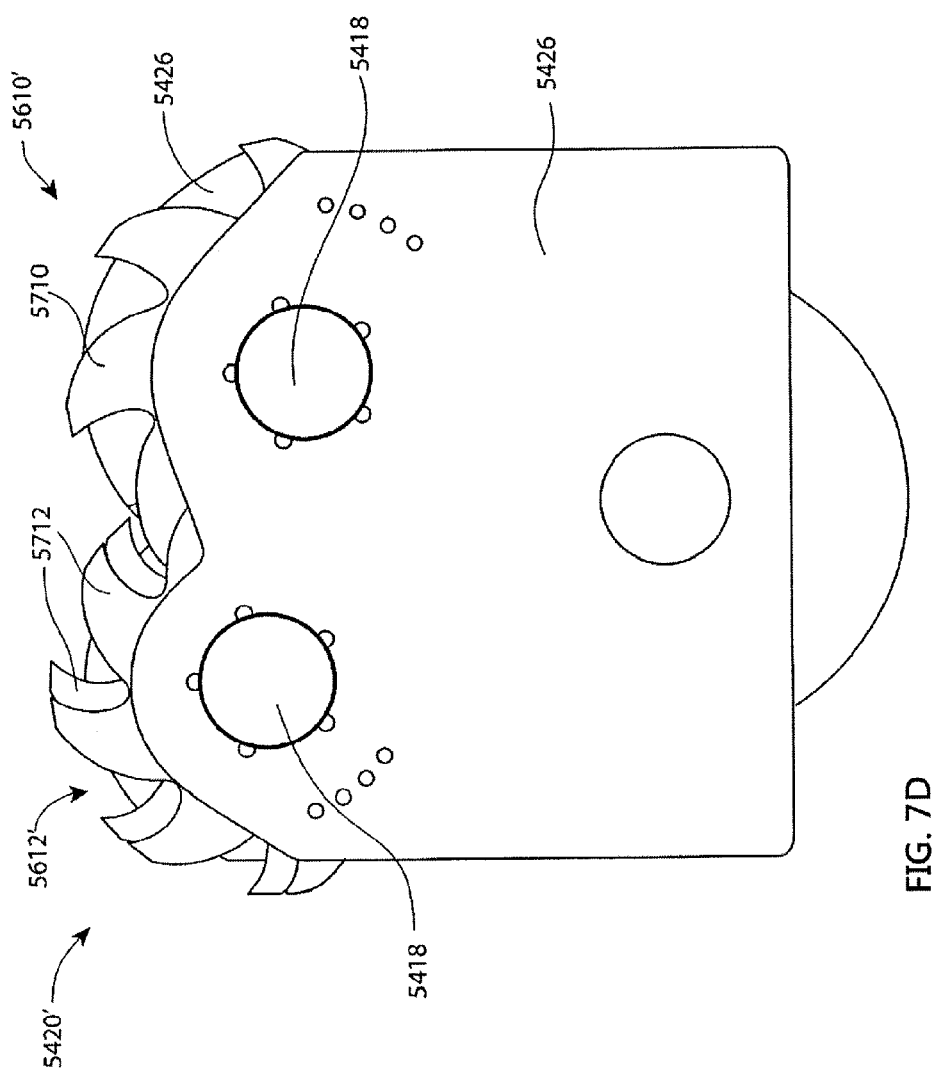
Figure 7E:
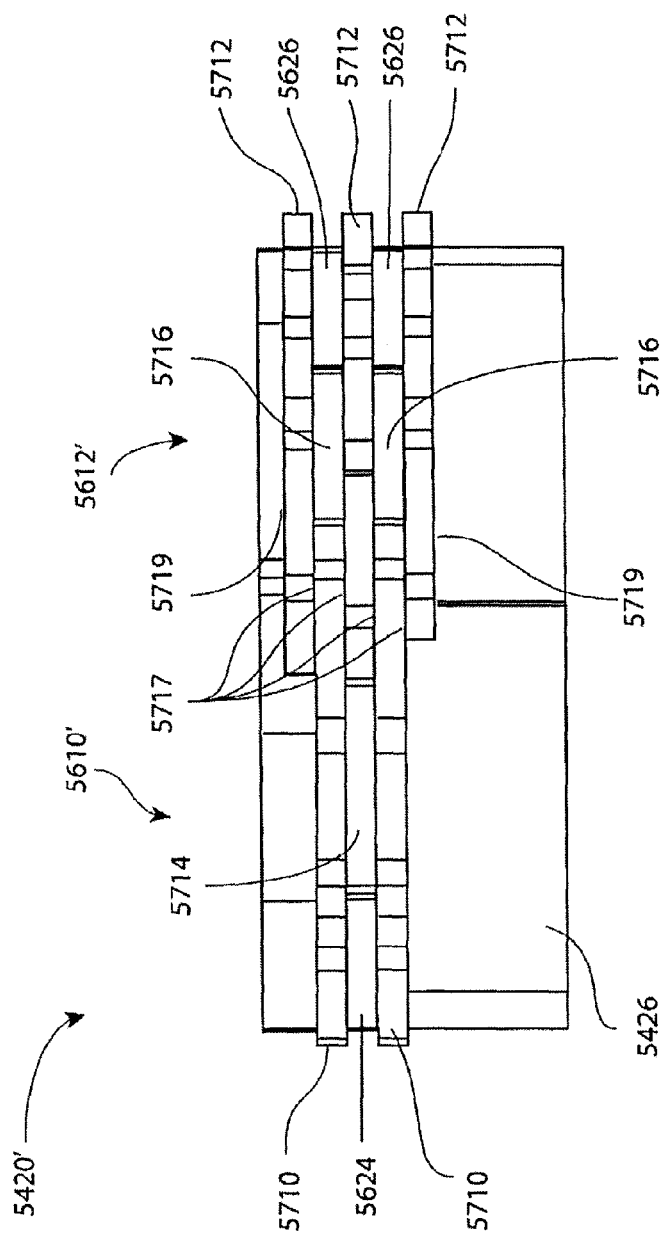

Referring to the top view shown in FIG. 7D, it can be seen that in this embodiment the axle 5418 of rotor 5612' is more distally located than axle 5418 of rotor 5610'. It can also be seen that while a top plate portion of rotor housing 5426 covers most of rotor blades 5710 and 5712, the blades protrude less from a middle and bottom plate portion of housing 5426. Further details of protruding blades and rotor characteristics are subsequently discussed in reference to FIG. 7F.

A front or distal end view is shown in FIG. 7G. As depicted in FIG. 7G, very small gaps or interference fits 5717 between overlapping blades 5710 and 5712 are desirable in some embodiments. Similarly, very small gaps or interference fits 5719 between blades 5712 and adjacent portions of rotor housing 5426 are desirable in some embodiments, as will be subsequently described in more detail.

Figure 7F:
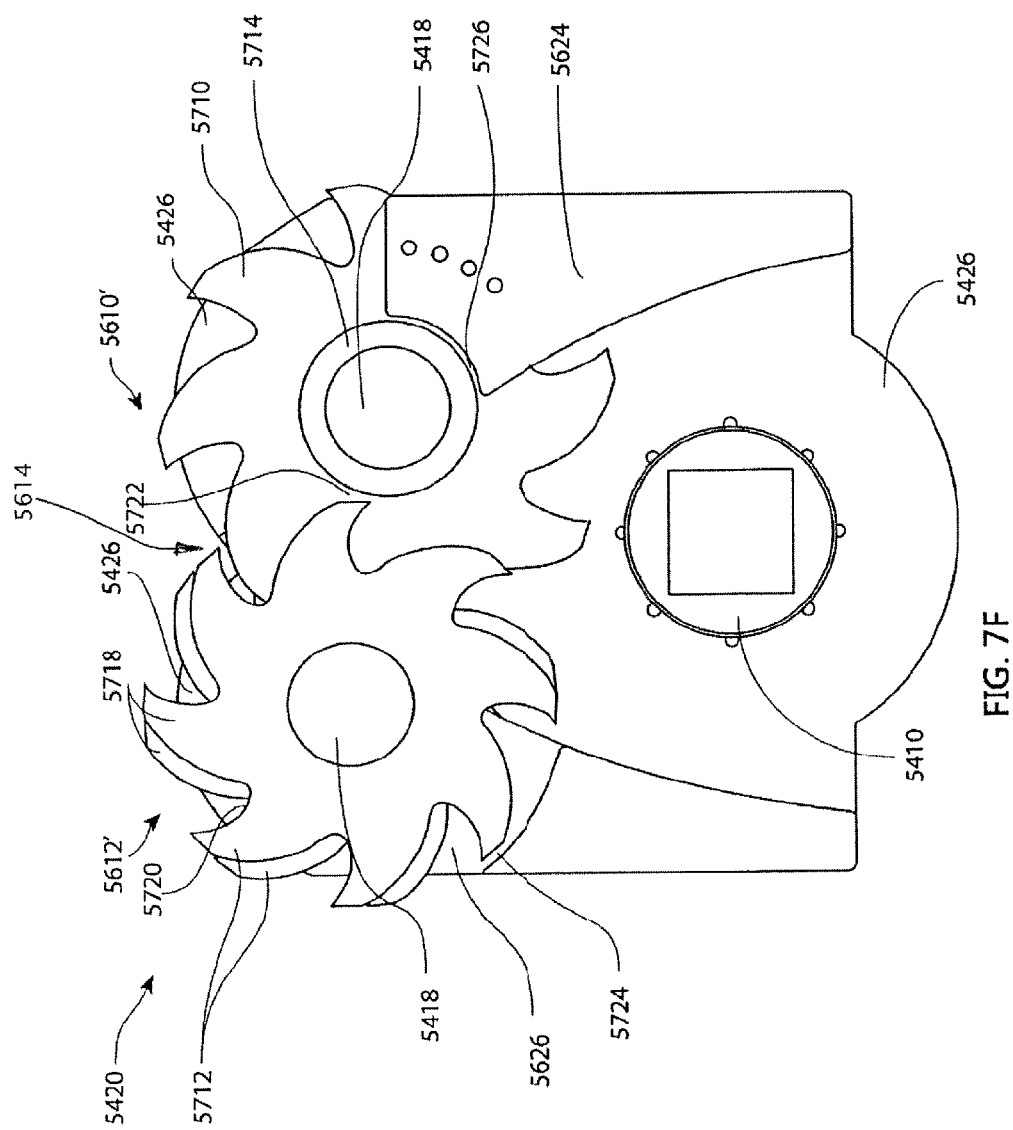

Referring to the cross-sectional plan view of FIG. 7F, the bottom two blades 5712 of rotor 5612' and the bottom blade 5710 of rotor 5610' are shown. As shown, blades 5710 have a larger outer diameter than that of blades 5712. But because axle 5418 of rotor 5612' is located more distally than axle 5418 of rotor 5610', blades 5712 protrude more distally from the bottom of rotor housing 5426 than do blades 5710 of rotor 5610'. It can also be seen that teeth 5718 and associated troughs 5720 of blades 5712 are configured to be rotationally out of phase with those of other blades 5712 of rotor 5612'. As will subsequently be discussed in more detail, this arrangement can tune rotors 5612 to selective cut certain types of tissue and avoid cutting other types of tissue.

Various rotor gaps can be seen in FIG. 7F. For example, gap 5722 is shown between the tips of blade teeth 5718 of rotor 5612' and spacer ring 5714/axle 5418 of opposing rotor 5610'. Gap 5724 is also shown, between the tips of blade teeth 5718 of rotor 5612' and the adjacent portion of housing 5426. Gap 5726 is also shown, between spacer ring 5714/axle 5418 of rotor 5610' and the adjacent portion of housing 5426. In some embodiments, it is desirable to keep gaps 5722, 5724 and 5726 very small, to ensure that tissue portions/particles that pass through rotors 5610' and 5612' are first cut to a very small size, and to avoid jamming or clogging rotors 5610' and 5612'. In some embodiments, these gaps are fabricated as small interferences between the adjacent parts so that when the rotors are first rotated, the adjacent parts hit each other and wear down or burnish each other. In this manner, after a break in period, smaller interference or zero clearance fits are created between the adjacent moving parts. Gap distances that applicants believe are advantageous include less than about 20 microns, less than about 10 microns, less than about 5 microns, less than about 1 micron, substantially zero, an initial interference fit of at least 2 microns, and an initial interference fit of about 5 microns.

In operation, the cutter elements of rotor housing assembly shown in FIGS. 7A-7F serve to grab tissue from a target source, draw the tissue towards a central region between the blades, cut the tissue from the source, and morcellate the tissue in small pieces for transport away from the body. In other embodiments, separate cutter elements may be used for these various functions. For example, one blade or blades may be used to cut tissue from the source, while another blade or set of blades may be used to morcellate the cut tissue.

Components of cutter head assembly 5332, including rotor housing assemblies 5420 and 5420', may be fabricated using processes such as laser cutting/machining, photo chemical machining (PCM), Swiss screw, electro-discharge machining (EDM), electroforming and/or other processes for fabricating small parts. Wafer manufacturing processes may be used to produce high precision micro parts, such as EFAB, X-ray LIGA (Lithography, Electroplating, and Molding), and/or UV LIGA. An electrochemical fabrication technique for forming three-dimensional structures from a plurality of adhered layers is being commercially pursued by applicant Microfabrica® Inc. (formerly MEMGen Corporation) of Van Nuys, Calif. under the name EFAB®. Such a technique may be advantageously used to fabricate components described herein, particularly rotors and associated components.

In some embodiments, the shredder's ability to selectively remove tissue is attributed to the protrusion of the rotating cutters from the housing and the design of a tooth pitch (space between the tips of adjacent teeth) of each rotor. In some embodiments, the protrusion sets the depth of the inward cut for the tips of the rotor. This inward depth controls the thickness of tissue being removed. The tooth pitch or number of teeth circumferentially about the rotor diameter provides an opening for individual tissue fibers and/or fiber bundles to be hooked, tensioned and drawn between the cutters.

From the point of view of the selected tissue, the tooth pitch and protrusion may be designed to grasp the smallest fibers or fiber bundles that are to be removed. From the point of view of the non-selected tissue, the tooth pitch may be many times smaller than the fiber or fiber bundle, and the protrusion may also be equally smaller than the fiber/bundle diameter.

As previously described, FIG. 7D shows the exemplary protrusion of blades 5710 and 5712 as viewed from the top of a rotor housing assembly 5420'. In some embodiments, the protrusion is more exposed on the top side than the bottom. In other embodiments, the cutter device has the same protrusion for both sides. Biasing the protrusion more on one side than the other can provide advantages such as cutting/shredding directionality and/or additional safety. Blade protrusion distances that applicants believe are advantageous include less than about 100 microns, less than about 10 microns, substantially flush with the housing, recessed a minimum of about 5 microns, and recessed a minimum of about 10 microns.

Tooth pitch is the distance from one tooth tip to the next tooth tip along an imaginary circle circumscribing the outer circumference of the blade. The trough diameter or depth generally is the distance between the tooth tip and the low point between the tooth tips. In many embodiments, the trough is a critical geometry component that enables tissue selectivity. Additionally, the trough opening (i.e. the distance from tooth tip to the tooth back of an adjoining tooth) can determine the size of the "window" for capturing a fiber or fiber bundle diameter.

In some embodiments, the target tissue being cut is hydrated and generally has a nominal fiber diameter of about 6 to about 9 microns. In some embodiments, the target tissue being cut is dry and generally has a nominal fiber diameter of about 5 to about 6 microns. In some embodiments, the tissue fibers are connected together in bundles having a nominal diameter of about 250 microns.

Typical dimensions in some embodiments include:
Housing diameter: 6 mm or less
Blade diameter range: 0.75 mm to 4 mm
Tip to Tip range: 0.2 mm to 1 mm
Trough diameter range: 2 microns to 0.5 mm
Blade protrusion range: 2 microns to 2 mm The tip to tip distance is typically at least two times the trough diameter for hook type teeth.

The tissue cutting devices disclosed herein may be configured for use in a variety of procedures. An example of a cardiac application is using the inventive devices to selectively remove endocardium, with the cutting device configured to leave the underlying myocardium uncut. An example of a tissue removing application involving the esophagus includes selectively removing mucosa, leaving the submucosa. Such a therapy would be useful for treating Barrett's disease. Examples in the spinal area include selectively removing flavum, with the cutting device configured to stop removing tissue when dura is reached, leaving the dura intact. Selective removal of flavum but not nerve root is another embodiment. A cutting device constructed according to aspects of the invention can also be configured to remove flavum without cutting bone. In this embodiment, the rotor velocity could be changed and/or the cutting elements could be changed after the flavum is removed such that some bone tissue could then be removed. Examples in the neurovascular area include selectively removing cancerous tissue while not cutting adjacent blood vessel tissue or nerve tissue. In the rheumatology field, tears in labral target tissue may be selectively removed while preserving adjacent non-target tissue, such as in the hips, shoulders, knees, ankles, and small joints. In some embodiments, small teeth on the rotors can interact with micron scale fibers of cartilage, removing tissue in a precise way, much like precision machining of materials that are harder than tissue. Other target tissues that may be selectively removed by the inventive devices and methods described herein include cartilage, which tends to be of a medium density, periosteum, stones, calcium deposits, calcified tissue, cancellous bone, cortical bone, plaque, thrombi, blood clots, and emboli.

It can be appreciated by those skilled in the art of tissue removal that soft tissue is much more difficult to remove in a small quantities and/or in a precise way than harder tissue such as bone that may be grinded or sculpted, since soft tissue tends to move or compress when being cut, rather than cut cleanly. Cutting tissue rather than removing it with a laser or other high energy device has the advantage of not overheating the tissue. This allows the tissue to be collected and its pathology tested, as previously described.

In some embodiments of the invention, the selective tissue cutting tool may be moved laterally along a tissue plane, removing thin swaths of tissue with each pass until the desired amount or type of tissue is removed. In some embodiments, the tool may be plunged into the target tissue in a distal direction, until a desired depth or type of tissue is reached. In any of these embodiments, the tool may cut a swath or bore that is as large as or larger than the width of the tool head. In some embodiments, the cutting elements are distally facing, laterally facing, or both.

Referring to FIGS. 8A-10C, further details of exemplary tissue cutting devices are depicted. For clarity of illustration and explanation, the rotors depicted in these figures are shown with only one or two blades each, and some of the blades include only a single hook-shaped tooth. Functional surgical instruments may be fabricated with these simplified constructs. However, the concepts being discussed relative to these embodiments may be equally applied to the other embodiments disclosed herein (e.g., rotors having many blades and/or multi-toothed blades.) Additionally, various portions of the rotors depicted in these figures may be shown as separate components for clarity. In some embodiments, these portions may be fabricated as separate components, while in other embodiments they may be integrally formed into unitary rotors.

Figure 8A:
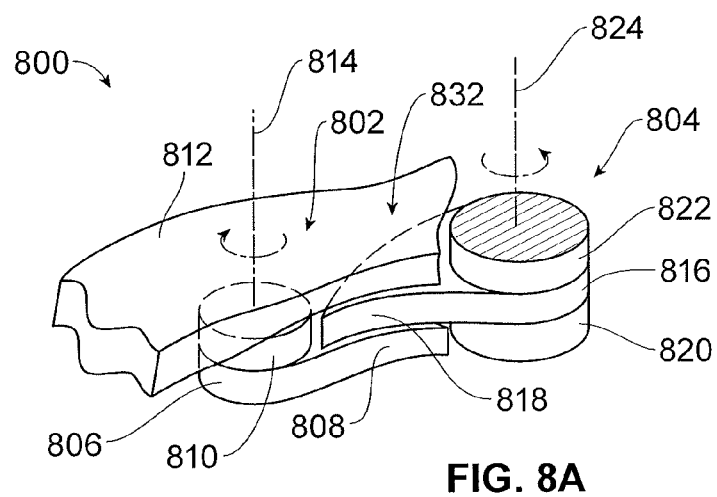
FIGS. 8A-8C show tissue shearing details of an exemplary two blade device.

Referring first to FIG. 8A, a tissue cutting device 800 having two overlapping or interdigitated rotatable members 802 and 804 is shown. First rotatable member 802 comprises a first hook-shaped blade 806 having a first tooth 808, and a first axle portion 810. First rotatable member 802 is rotatably mounted to housing 812 such that it rotates about a first axis 814. Second rotatable member 804 comprises a second hook-shaped blade 816 having a second tooth 818, a second axle portion 820, and a third axle portion 822. Second rotatable member 804 is rotatably mounted to housing 812 such that it rotates about a second axis 824 that is parallel and offset from first axis 814. A portion of housing 812 resides directly adjacent to second blade 816 (shown above second blade 816 in FIG. 8A.)

First blade 806 and second axle portion 820 both lie in a first plane 826, and may be fabricated in the same layer(s)/processing step(s), for example if a MEMS fabrication process is used. Similarly, second blade 816 and first axle portion 810 both lie in a second plane 828, and may be fabricated in the same layer(s)/processing step(s). Additionally, third axle portion 820 and housing portion 812 both lie in a third plane 830, and may be fabricated in the same layer(s)/processing step(s). Regardless of whether a MEMS fabrication process is used, first blade 806 and first axle portion 810 of first rotatable member 802 may be formed as separate, discrete components or may be formed to create an integrated, monolithic structure. Similarly, second blade 816, second axle portion 820 and third axle portion 822 of second rotatable member 804 may be formed as separate, discrete components or may be formed to create an integrated, monolithic structure.

Figure 8B:
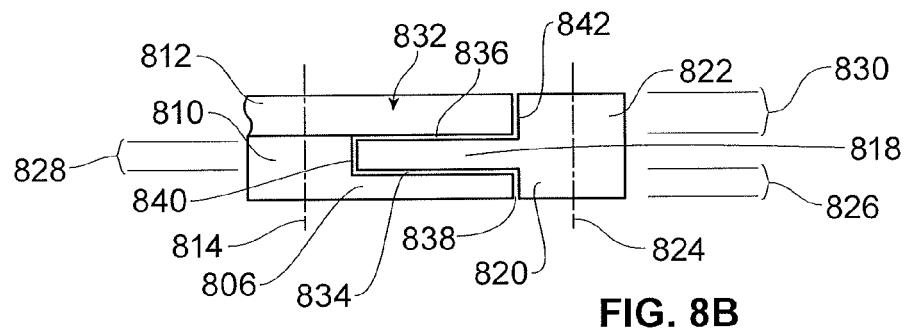
Figure 8C:
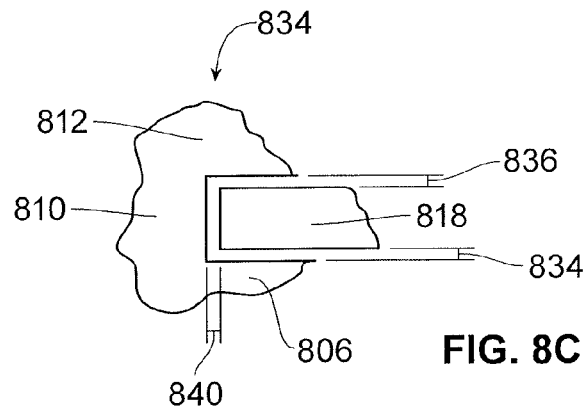

As can be seen in FIGS. 8A and 8B, there is a region of overlap 832 that generally lies between first axis 814 and second axis 824 in which first blade 806 and second blade 816 overlap one another. In some embodiments, first blade 806 and second blade 816 are always overlapping. In other embodiments, such as shown in FIGS. 8A-8C, first blade 806 and second blade 816 only overlap during one or more portions of their rotations, such as when first tooth 808 and second tooth 818 both rotate into the region of overlap 832 simultaneously. In this embodiment, first rotatable member 802 and second rotatable member 804 rotate at the same angular velocity and are synchronized so that first tooth 808 and second tooth 818 overlap one another each time they pass through the region of overlap 832. Additionally, housing portion 812 overlaps second blade 816, at least in the region of overlap 832 when second tooth 818 passes through.

Referring to FIGS. 8B and 8C, the overlapping relationship between first blade 806, second blade 816 and housing portion 812 can be seen. A small gap 834 is provided between first blade 806 and second blade 816. Similarly, a small gap 836 is provided between second blade 816 and housing portion 812. The outer circumference of first blade 806 and the diameter of second axle portion 820 are selected relative to the spacing of first rotation axis 814 and second rotation axis 824 such that a small gap 838 is provided between the tip of first tooth 808 and second axle portion 820. Similarly, the outer circumference of second blade 816 and the diameter of first axle portion 810 are selected relative to the spacing of first rotation axis 814 and second rotation axis 824 such that a small gap 840 is provided between the tip of second tooth 818 and first axle portion 810. A gap 842 is also provided between third axle portion 822 and housing portion 812.

Gap 834 is kept small so that tissue can be efficiently sheared between first tooth 808 and second tooth 818. Similarly, gap 836 is kept small so that tissue can be efficiently sheared between second tooth 818 and housing portion 812. Gap 838 is kept small so that tissue can be efficiently sheared between the tip of first tooth 808 and second axle portion 820. Gap 840 is kept small so that tissue can be efficiently sheared between the tip of second tooth 818 and first axle portion 810. Gap 842 is kept small so that tissue can be efficiently sheared between third axle portion 822 and housing portion 812.

What is meant by "small gap" is a tight interface between mating surfaces or edges, which in some embodiments is essentially no gap at all. In these embodiments, mating parts may be configured such that the gap is so small that it is not measurable. This may be accomplished by creating a sliding fit between the mating parts, or creating a small interference fit. With an interference fit, the parts may be designed to flex away from each other so they do not bind. In some embodiments, an interference fit can be reduced to a zero gap fit by driving the rotors with high torque during a break-in period to allow the surfaces to wear or burnish against each other to remove a small amount of material. In some embodiments, at least one of the gaps 834 and 836 is no more than 30 microns. In some embodiments, at least one of the gaps 838, 840 and 842 is no more than 30 microns. In some embodiments, all of the gaps 834, 836, 838, 840 and 842 are no more than 30 microns.

The combination of the five tissue shearing interfaces provided around a blade as just described allows tissue to be sheared more quickly, efficiently and predictably. When all gaps are kept very small, tissue may be efficiently sheared into small pieces (as will be subsequently described in more detail) around all surfaces of the blade, with a reduced risk of the rotatable members getting clogged or jammed.

Figure 9A:
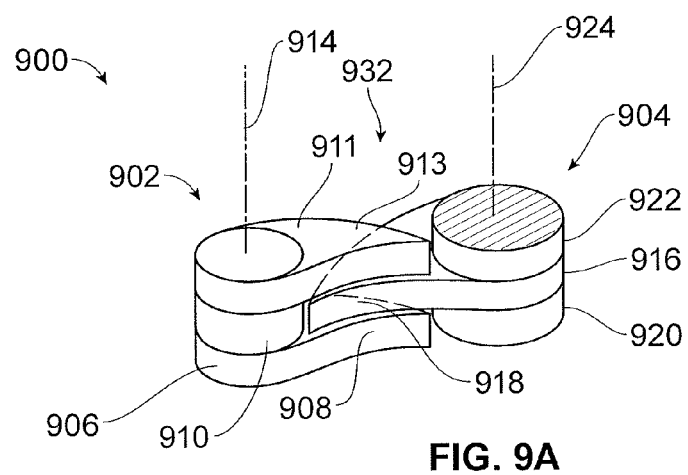
FIGS. 9A-9C show tissue shearing details of an exemplary three blade device.
Figure 9B:
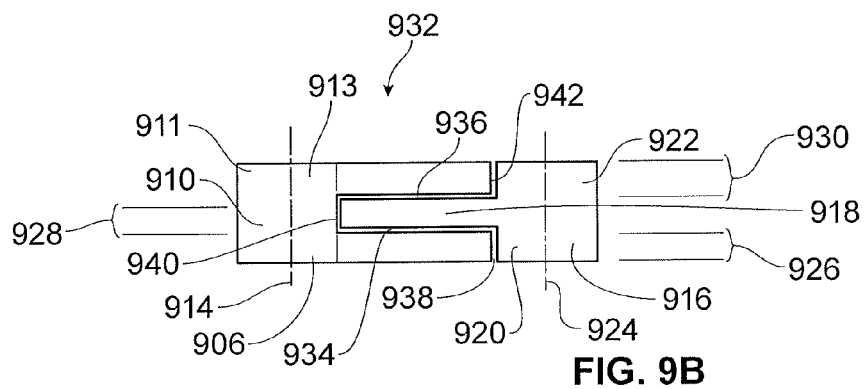
Figure 9C:
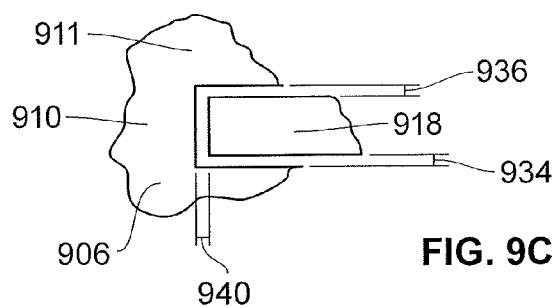

Referring to FIGS. 9A-9C, another embodiment similar to that shown in FIGS. 8A-8C will be described. In this embodiment, one of the rotatable members has more than one blade.

Referring first to FIG. 9A, a tissue cutting device 900 having two overlapping or interdigitated rotatable members 902 and 904 is shown. First rotatable member 902 comprises a first hook-shaped blade 906 having a first tooth 908, a first axle portion 910, and a third hook-shaped blade 911 having a third tooth 913. First rotatable member 902 is rotatably mounted to a housing (not shown) such that it rotates about a first axis 914. Second rotatable member 904 comprises a second hook-shaped blade 916 having a second tooth 918, a second axle portion 920, and a third axle portion 922. Second rotatable member 904 is rotatably mounted to the housing such that it rotates about a second axis 924 that is parallel and offset from first axis 914.

First blade 906 and second axle portion 920 both lie in a first plane 926, and may be fabricated in the same layer(s)/processing step(s), for example if a MEMS fabrication process is used. Similarly, second blade 916 and first axle portion 910 both lie in a second plane 928, and may be fabricated in the same layer(s)/processing step(s). Additionally, third blade 911 and third axle portion 920 both lie in a third plane 930, and may be fabricated in the same layer(s)/processing step(s). Regardless of whether a MEMS fabrication process is used, first blade 906, first axle portion 910, and third blade 911 of first rotatable member 902 may be formed as separate, discrete components or may be formed to create an integrated, monolithic structure. Similarly, second blade 916, second axle portion 920 and third axle portion 922 of second rotatable member 904 may be formed as separate, discrete components or may be formed to create an integrated, monolithic structure.

As can be seen in FIGS. 9A and 9B, there is a region of overlap 932 that generally lies between first axis 914 and second axis 924 in which first blade 906, second blade 916 and third blade 911 overlap one another. In some embodiments, first blade 906, second blade 916 and third blade 911 are always overlapping. In other embodiments, such as shown in FIGS. 9A-9C, first blade 906, second blade 916 and third blade 911 only overlap during one or more portions of their rotations, such as when first tooth 908, second tooth 918 and third tooth 913 all rotate into the region of overlap 932 simultaneously. In this embodiment, first rotatable member 902 and second rotatable member 904 rotate at the same angular velocity and are synchronized so that first tooth 908, second tooth 918 and third tooth 913 overlap one another each time they pass through the region of overlap 932.

Referring to FIGS. 9B and 9C, the overlapping relationship between first blade 906, second blade 916 and third blade 911 can be seen. A small gap 934 is provided between first blade 906 and second blade 916. Similarly, a small gap 936 is provided between second blade 916 and third blade 911. The outer circumference of first blade 906 and the diameter of second axle portion 920 are selected relative to the spacing of first rotation axis 914 and second rotation axis 924 such that a small gap 938 is provided between the tip of first tooth 908 and second axle portion 920. Similarly, the outer circumference of second blade 916 and the diameter of first axle portion 910 are selected relative to the spacing of first rotation axis 914 and second rotation axis 924 such that a small gap 940 is provided between the tip of second tooth 918 and first axle portion 910. Additionally, the outer circumference of third blade 911 and the diameter of third axle portion 922 are selected relative to the spacing of first rotation axis 914 and second rotation axis 924 such that a small gap 942 is provided between the tip of third tooth 913 and third axle portion 922.

Gap 934 is kept small so that tissue can be efficiently sheared between first tooth 908 and second tooth 918. Similarly, gap 936 is kept small so that tissue can be efficiently sheared between second tooth 918 and third tooth 911. Gap 938 is kept small so that tissue can be efficiently sheared between the tip of first tooth 908 and second axle portion 920. Gap 940 is kept small so that tissue can be efficiently sheared between the tip of second tooth 918 and first axle portion 910. Gap 942 is kept small so that tissue can be efficiently sheared between third tooth 913 and third axle portion 922.

What is meant by "small gap" is a tight interface between mating surfaces or edges, which in some embodiments is essentially no gap at all. In these embodiments, mating parts may be configured such that the gap is so small that it is not measurable. This may be accomplished by creating a sliding fit between the mating parts, or creating a small interference fit. With an interference fit, the parts may be designed to flex away from each other so they do not bind. In some embodiments, a "negative gap" or interference fit can be reduced to a zero gap fit by driving the rotors with high torque during a break-in period to allow the surfaces to wear or burnish against each other to remove a small amount of material. In some embodiments, at least one of the gaps 934 and 936 is no more than 30 microns. In some embodiments, at least one of the gaps 938, 940 and 942 is no more than 30 microns. In some embodiments, all of the gaps 934, 936, 938, 940 and 942 are no more than 30 microns.

Additional blades may be added to rotatable members 902 and 904 such that each member has three or more blades, with the blades of the first rotatable member 902 interdigitated with the blades of the second rotatable member 902. With all gaps between the blades, axle portions and housing kept small (no more than 30 microns in some embodiments), tissue may be drawn into the housing and efficiently sheared into small pieces with a reduced risk of the rotatable members getting clogged or jammed.

Figure 10A:
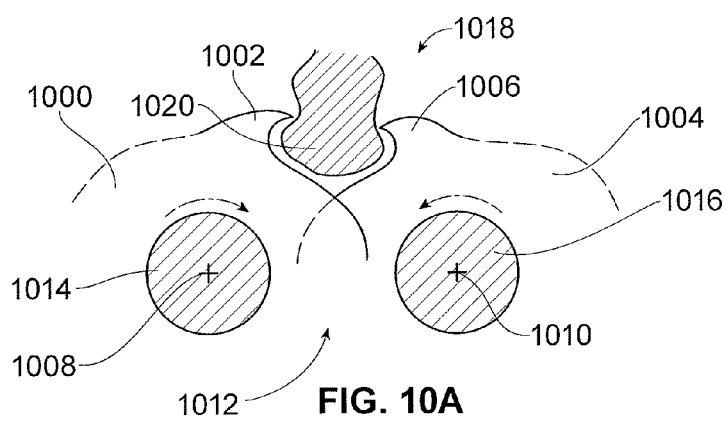
FIGS. 10A-10C show further tissue shearing details.
Figure 10B:
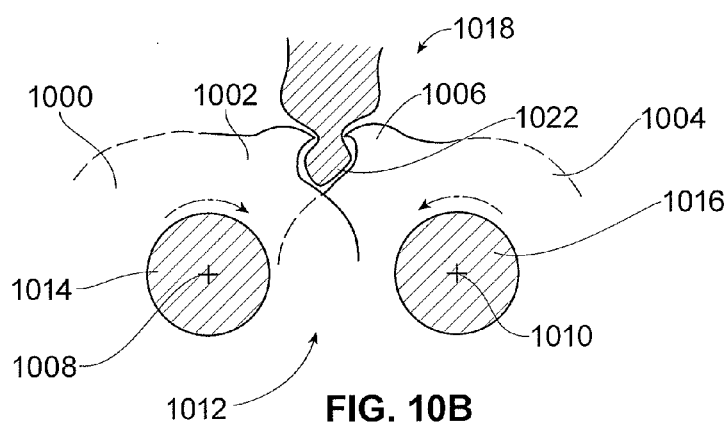
Figure 10C:
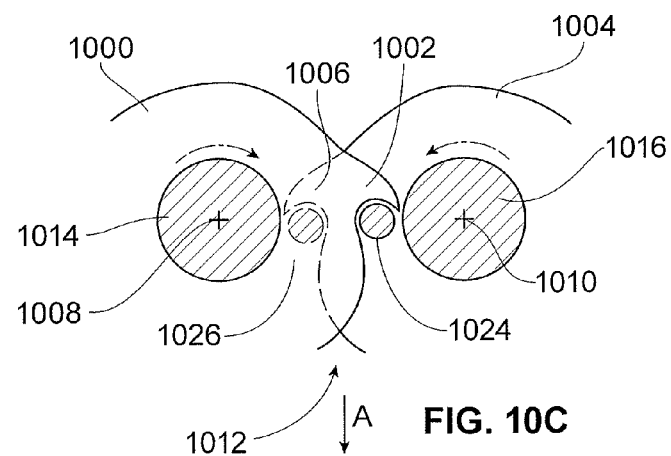

Referring to FIGS. 10A-10C, additional details of the tissue shearing process of some embodiments will be described. The exemplary embodiment shown in these figures includes a first blade 1000 having a first tooth 1002, and a second blade 1004 having a second tooth 1006. First blade rotates about a first axis 1008, and second blade 1004 rotates about a second axis 1010 that is parallel to and radially offset from first axis 1008. First blade 1000 partially overlaps with second blade 1004 in an overlap region 1012. First blade 1000 lies in a plane directly above second blade 1004 with a small gap therebetween, as with previously described embodiments. First blade 1000 has a first axle portion 1014 directly below it, in the same plane as second blade 1004. Similarly, second blade 1004 has a second axle portion 1016 directly above it, in the same plane as first blade 1000.

FIGS. 10A-10C show a progression of steps that occur when the first and second blades cut tissue 1018 into small pieces. As shown in FIG. 10A, first tooth 1002 and second tooth 1006 initially engage the target tissue 1018 when the teeth are near the outer reach of their orbits closest to the tissue. Teeth 1002 and 1006 grab the tissue and start to compress it as they travel toward each other. As shown in FIG. 10A, a heart-shaped volume of tissue 1020 is engaged by the teeth. As teeth 1002 and 1006 travel closer together as shown in FIG. 10B, the heart-shaped volume of tissue is further compressed into a generally circular shaped piece of tissue 1022. As the tips of the teeth come closer together, this circular volume 1022 is separated from the main tissue mass 1018. As shown in FIG. 10C, tooth 1002 of first blade 1000 passes over second blade 1004 and shears the compressed, circular tissue volume in half against the second blade 1004, forming a first thin disc of tissue 1024. The outer tip of first tooth 1002 comes close to the outer diameter of second axle portion 1016 (within 30 microns or less in some embodiments, as previously described.) Any portion of tissue disc 1024 that may be hanging over the tip of the first tooth 1002 is then sheared between the tip and second axle portion 1016. In a similar manner, tooth 1006 of second blade 1004 passes over first blade 1000 and shears the compressed, circular tissue volume in half against the first blade 1000, forming a second thin disc of tissue 1026. The outer tip of second tooth 1006 comes close to the outer diameter of first axle portion 1014 (within 30 microns or less in some embodiments, as previously described.) Any portion of tissue disc 1026 that may be hanging over the tip of the second tooth 1006 is then sheared between the tip and first axle portion 1014. As teeth 1002 and 1006 continue to rotate past the overlap region 1012, tissue discs 1024 and 1026 and other smaller pieces of tissue are expelled into the center of the housing, in the direction of Arrow A. It can be appreciated that when many blades are stacked up and interdigitated like the two blades shown in FIGS. 10A-10C, a target tissue volume 1018 may be quickly rendered into many small discs of tissue.

In some embodiments, the diameter of tissue discs 1024 and 1026 is no larger than about 3000 microns. In other embodiments, the diameter of tissue discs 1024 and 1026 is no larger than about 750 microns. In other embodiments, the diameter of tissue discs 1024 and 1026 is no larger than about 150 microns. In some embodiments, the thickness of tissue discs 1024 and 1026 is no larger than about 1000 microns. In other embodiments, the thickness of tissue discs 1024 and 1026 is no larger than about 250 microns. In other embodiments, the thickness of tissue discs 1024 and 1026 is no larger than about 50 microns. In some embodiments, the small pieces of tissue expand as they are released from teeth 1002 and 1006. In other embodiments, the small pieces of tissue have had liquid compressed out of them and do not expand appreciably. It can be appreciated that when the profiles of first tooth 1002 and second tooth 1006 are modified, the shape of the tissue pieces that emerge may be other than disc shaped.

While exemplary embodiments have been shown having teeth on opposing rotatable members that rotate in sync with one another, in other embodiments the teeth may be arranged so that they are out of sync with one another. In other words, a tooth from one blade may shear tissue with a portion of an opposing blade where there is no tooth, and vice versa. In some embodiments, the rotations of the first and the second rotatable members are configured to alternately rotate in and out of phase with one another. This may be accomplished, for example, by independently driving the rotatable members with separate motors and/or drive trains, by driving two similar rotatable members at different speeds, or driving two dissimilar rotatable members at the same speed.

In some embodiments the first and the second rotatable members are configured to periodically reverse direction of rotation during tissue cutting. This may be done to ensure the tissue cutting head does not clog, to disengage the cutting head from the target tissue, or to engage a different portion of the target tissue, for example. Cutting teeth may be provided that cut equally well in both directions, or are optimized for cutting in a single direction. The rotations of the first and the second rotatable members may be configured to reverse direction at least once per second. In some embodiments the device is configured to provide a dwell time of at least about 50 milliseconds when the first and the second rotatable members reverse direction.

In view of the teachings herein, many further embodiments, alternatives in design and uses of the embodiments of the instant invention will be apparent to those of skill in the art. As such, it is not intended that the invention be limited to the particular illustrative embodiments, alternatives, and uses described above but instead that it be defined by the claims presented hereafter.

What is claimed is:

1. A medical device for removing tissue from a subject, comprising:
    a distal housing configured with at least one tissue engaging opening;
    an elongate member coupled to the distal housing and configured to introduce the distal housing to a target tissue site of the subject;

a first rotatable member located at least partially within the distal housing and configured to rotate about a first axis, the first rotatable member comprising a first disc-shaped blade having a series of teeth along an outer circumference of the blade, the first blade lying in a first plane; the first rotatable member further comprising a circular first axle portion lying in a second plane that is offset from, parallel and adjacent to the first plane, the first axle portion having an outer circumference that is smaller than that of the first blade, and a second rotatable member located at least partially within the distal housing and configured to rotate about a second axis parallel to and radially offset from the first axis, the second rotatable member configured to rotate in a direction opposite of a direction of rotation of the first rotatable member, the second rotatable member comprising a second disc-shaped blade having a series of teeth along an outer circumference of the blade, the second blade lying in the second plane, the second rotatable member further comprising a circular second axle portion lying in the first plane, the second axle portion having an outer circumference that is smaller than that of the second blade, wherein the first and second blades are directly adjacent to one another and positioned to partially overlap such that tissue may be sheared between the first and second blades, between the first blade and the second axle portion and between the second blade and the first axle portion, the rotatable members configured to engage tissue from the target tissue site with the teeth of the first and second blades, rotate towards one another and inwardly to direct tissue from the target tissue site through the tissue engaging opening and into an interior portion of the distal housing, wherein the distal housing further comprises a tissue cutting portion lying in a third plane that is offset from, parallel and adjacent to the second plane, wherein the tissue cutting portion and the second blade are directly adjacent to one another and positioned to partially overlap such that tissue may be sheared between the tissue cutting portion of the distal housing and the second blade.

2. The medical device of claim 1, wherein the first and second blades are no more than 30 microns apart where they partially overlap.

3. The medical device of claim 1, wherein the outer circumference of the first blade is no more than 30 microns apart from the outer circumference of the second axle portion, and the outer circumference of the second blade is no more than 30 microns apart from the outer circumference of the first axle portion.

4. The medical device of claim 1, where the first and the second blades and the first and the second axle portions each have a thickness of less than 1 mm.

5. The medical device of claim 1, wherein the first and second rotation axes are generally perpendicular to a longitudinal axis of the elongate member.

6. The medical device of claim 1, wherein the rotations of the first and the second rotatable members are synchronized such that a first trough associated with one of the teeth located along the outer circumference of the first blade and a second trough associated with one of the teeth located along the outer circumference of the second blade simultaneously engage a single fiber or single bundle of fibers from the target tissue site.

7. The medical device of claim 6, wherein the first and the second troughs cooperate to compress portions of the single fiber or single bundle of fibers as the first and the second rotatable members rotate toward one another, thereby reducing the volume of the tissue entering the distal housing.

8. The medical device of claim 1, wherein the first and the second rotatable members are independently driven.

9. A method of fabricating the device of claim 1, comprising fabricating the first blade and the second axle portion together in a first material deposition process step and fabricating the second blade and the first axle portion together in a second material deposition process step.

10. A method of using the device of claim 1, comprising urging the distal housing of the device against a target tissue site of a subject and extracting cut tissue pieces from a proximal end of the elongate member.

11. A medical device for removing tissue from a subject, comprising:
a distal housing configured with at least one tissue engaging opening;
an elongate member coupled to the distal housing and configured to introduce the distal housing to a target tissue site of the subject;
a first rotatable member located at least partially within the distal housing and configured to rotate about a first axis, the first rotatable member comprising a first disc-shaped blade having a series of teeth along an outer circumference of the blade, the first blade lying in a first plane; the first rotatable member further comprising a circular first axle portion lying in a second plane that is offset from, parallel and adjacent to the first plane, the first axle portion having an outer circumference that is smaller than that of the first blade, and
a second rotatable member located at least partially within the distal housing and configured to rotate about a second axis parallel to and radially offset from the first axis, the second rotatable member configured to rotate in a direction opposite of a direction of rotation of the first rotatable member, the second rotatable member comprising a second disc-shaped blade having a series of teeth along an outer circumference of the blade, the second blade lying in the second plane, the second rotatable member further comprising a circular second axle portion lying in the first plane, the second axle portion having an outer circumference that is smaller than that of the second blade,
wherein the first and second blades are directly adjacent to one another and positioned to partially overlap such that tissue may be sheared between the first and second blades, between the first blade and the second axle portion and between the second blade and the first axle portion, the rotatable members configured to engage tissue from the target tissue site with the teeth of the first and second blades, rotate towards one another and inwardly to direct tissue from the target tissue site through the tissue engaging opening and into an interior portion of the distal housing,
wherein the rotations of the first and the second rotatable members are configured to alternately rotate in and out of phase with one another.

12. A medical device for removing tissue from a subject, comprising:
a distal housing configured with at least one tissue engaging opening;

an elongate member coupled to the distal housing and configured to introduce the distal housing to a target tissue site of the subject;

a first rotatable member located at least partially within the distal housing and configured to rotate about a first axis, the first rotatable member comprising a first disc-shaped blade having a series of teeth along an outer circumference of the blade, the first blade lying in a first plane; the first rotatable member further comprising a circular first axle portion lying in a second plane that is offset from, parallel and adjacent to the first plane, the first axle portion having an outer circumference that is smaller than that of the first blade, and a second rotatable member located at least partially within the distal housing and configured to rotate about a second axis parallel to and radially offset from the first axis, the second rotatable member configured to rotate in a direction opposite of a direction of rotation of the first rotatable member, the second rotatable member comprising a second disc-shaped blade having a series of teeth along an outer circumference of the blade, the second blade lying in the second plane, the second rotatable member further comprising a circular second axle portion lying in the first plane, the second axle portion having an outer circumference that is smaller than that of the second blade, wherein the first and second blades are directly adjacent to one another and positioned to partially overlap such that tissue may be sheared between the first and second blades, between the first blade and the second axle portion and between the second blade and the first axle portion, the rotatable members configured to engage tissue from the target tissue site with the teeth of the first and second blades, rotate towards one another and inwardly to direct tissue from the target tissue site through the tissue engaging opening and into an interior portion of the distal housing, wherein the first and the second rotatable members are configured to periodically reverse direction of rotation during tissue cutting.

13. The medical device of claim 12, wherein the rotations of the first and the second rotatable members are configured to reverse direction at least once per second.

14. The medical device of claim 12, wherein the device is configured to provide a dwell time of at least about 50 milliseconds when the first and the second rotatable members reverse direction.

* * * * *